United States Patent
Witt et al.

(10) Patent No.: US 9,335,309 B2
(45) Date of Patent: May 10, 2016

(54) FLUIDIC VALVE WITH SELECTIVELY SWITCHABLE STORAGE PATHS

(75) Inventors: Klaus Witt, Waldbronn (DE); Konstantin Choikhet, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/411,276

(22) PCT Filed: Jun. 26, 2012

(86) PCT No.: PCT/EP2012/062394
§ 371 (c)(1),
(2), (4) Date: Dec. 24, 2014

(87) PCT Pub. No.: WO2014/000778
PCT Pub. Date: Jan. 3, 2014

(65) Prior Publication Data
US 2015/0204828 A1 Jul. 23, 2015

(51) Int. Cl.
| | | |
|---|---|---|
| *G01N 33/00* | (2006.01) | |
| *G01N 30/80* | (2006.01) | |
| *G01N 30/20* | (2006.01) | |
| *G01N 27/447* | (2006.01) | |
| *G01N 30/06* | (2006.01) | |
| *B01D 15/18* | (2006.01) | |
| *G01N 30/46* | (2006.01) | |
| *G01N 30/60* | (2006.01) | |

(52) U.S. Cl.
CPC .............. *G01N 30/80* (2013.01); *G01N 27/447* (2013.01); *G01N 30/06* (2013.01); *G01N 30/20* (2013.01); *B01D 15/1871* (2013.01); *G01N 30/461* (2013.01); *G01N 30/6039* (2013.01); *G01N 2030/208* (2013.01)

(58) Field of Classification Search
CPC .............................. G01N 30/80; G01N 30/20
See application file for complete search history.

(56) References Cited

U.S. PATENT DOCUMENTS

2012/0240666 A1 * 9/2012 Sims .................... G01N 30/463
73/61.56

FOREIGN PATENT DOCUMENTS

| CN | 102253159 A | 11/2011 |
|---|---|---|
| EP | 1457774 | 9/2004 |
| EP | 1536228 | 6/2005 |
| WO | WO2008150763 | 12/2008 |

OTHER PUBLICATIONS

International Search Report and Written Opinion mailed May 23, 2013 in International Patent Application No. PCT/EP2012/062394.
Office action dated Nov. 13, 2015 from related Chinese Application No. 201280074316.4.

* cited by examiner

*Primary Examiner* — Sam P Siefke

(57) ABSTRACT

A sample separation apparatus includes a fluidic valve including a first inlet fluidically coupled to one of a first fluid drive and a second fluid drive, and a second inlet fluidically coupled to the other of the first fluid drive and the second fluid drive. The fluidic valve includes at least two different sets of storage paths, wherein each set of storage paths comprises a first storage path. The first storage path of a first set of said at least two sets of storage paths has a first volume, and the first storage path of a second set of said at least two sets of storage paths has a second volume different from the first volume. The fluidic valve is configured for selectively switching one set of the least two sets of storage paths to the first inlet and the second inlet.

24 Claims, 10 Drawing Sheets

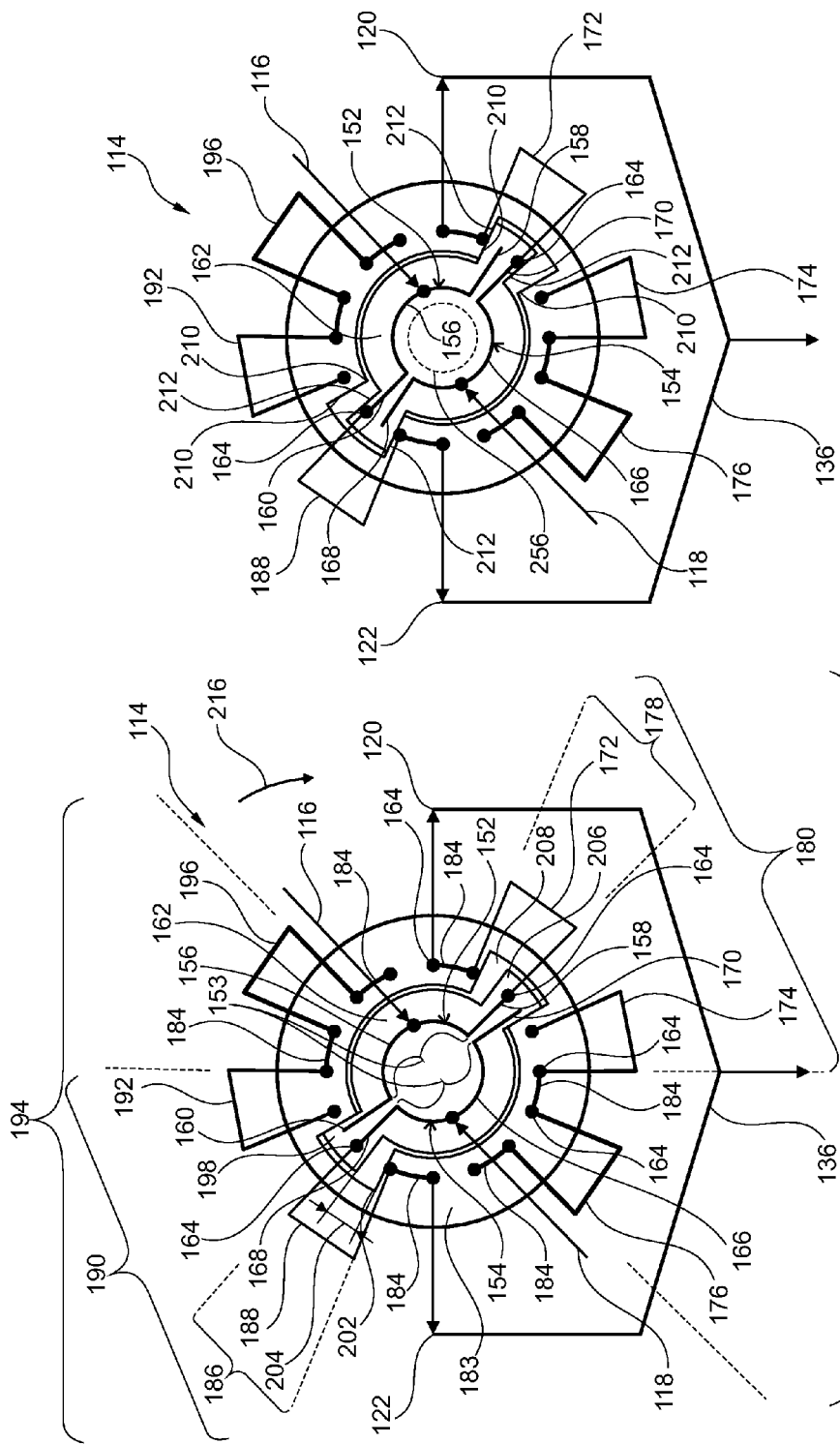

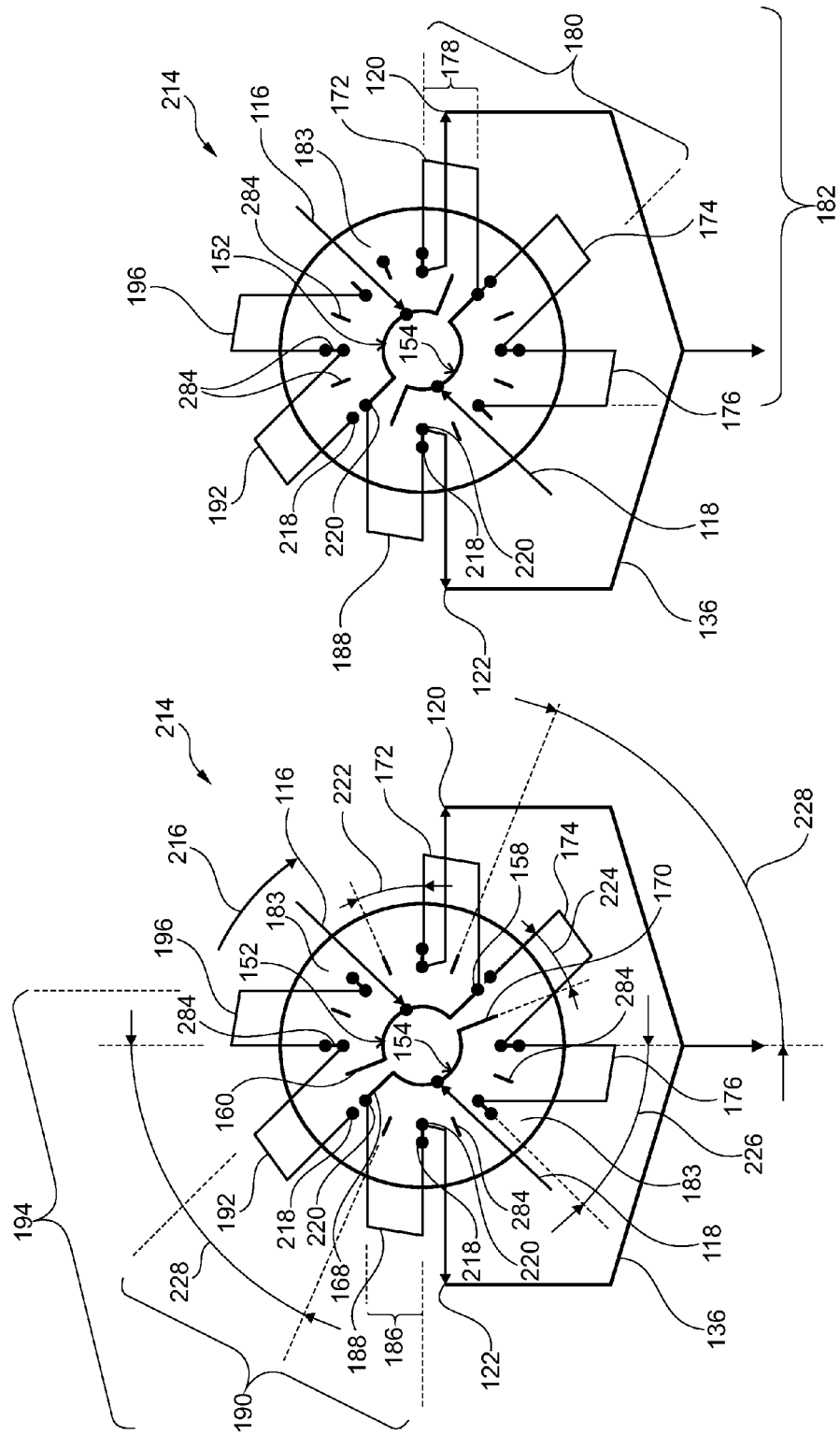

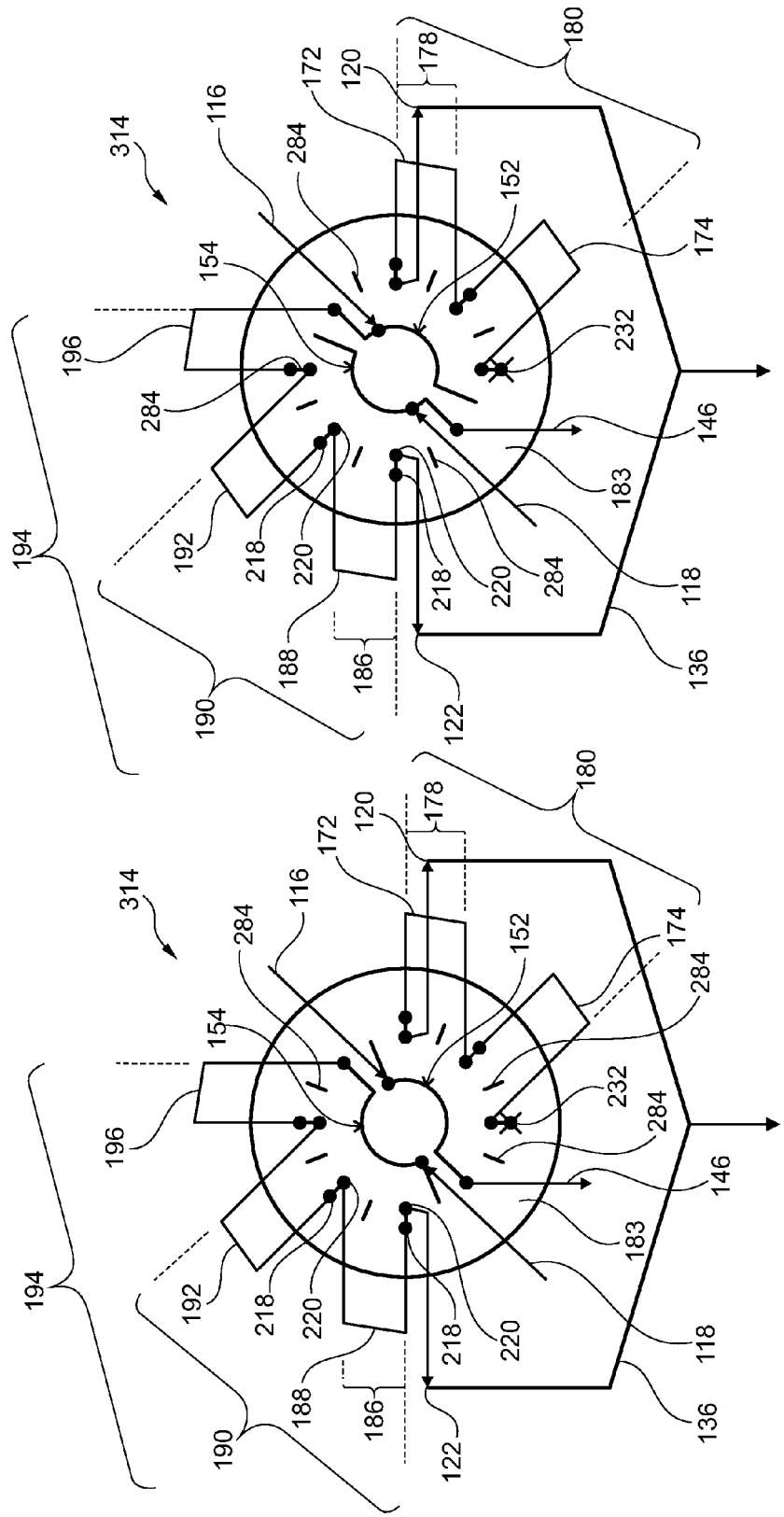

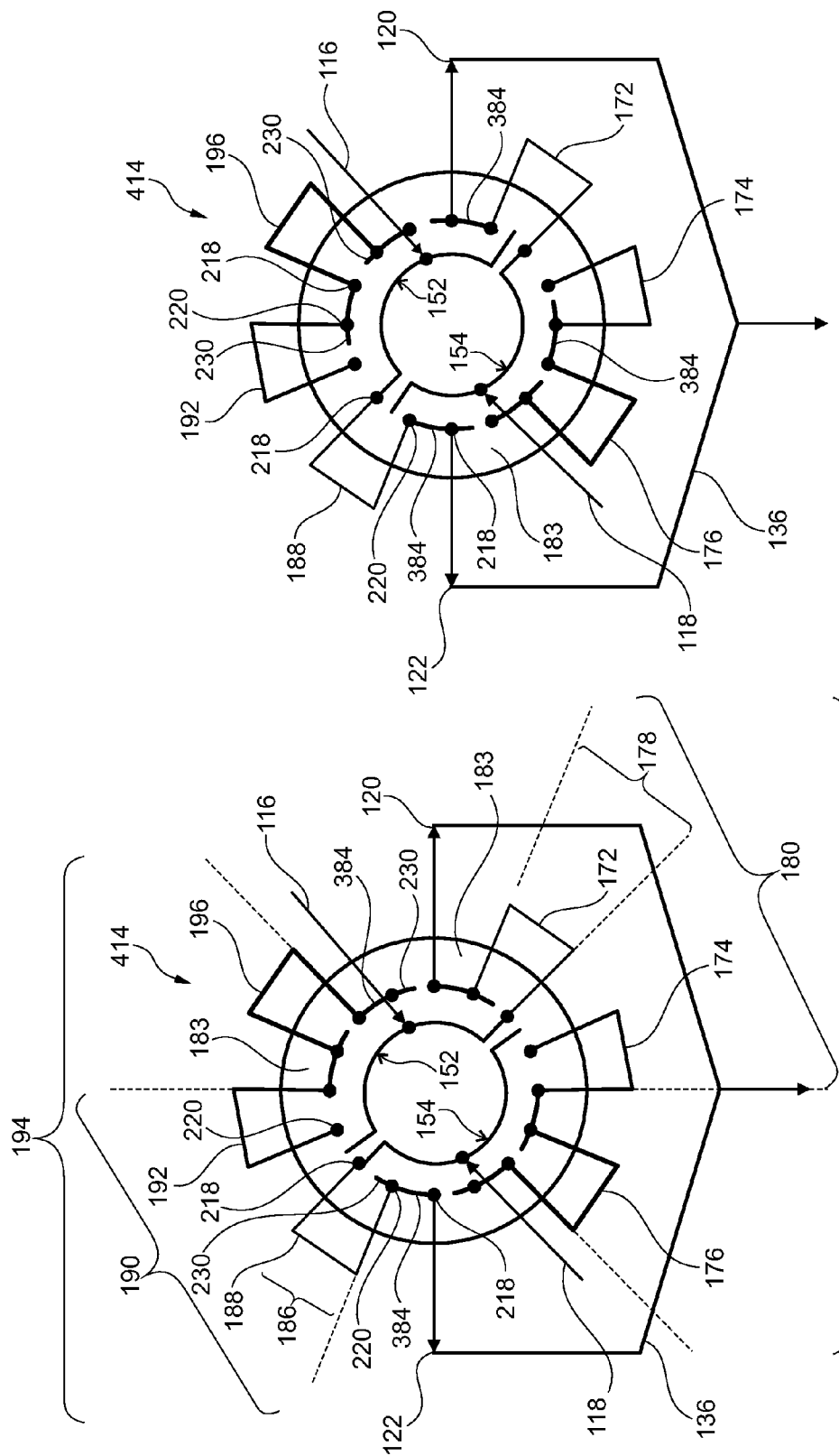

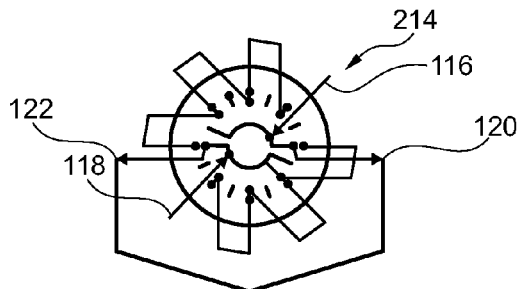
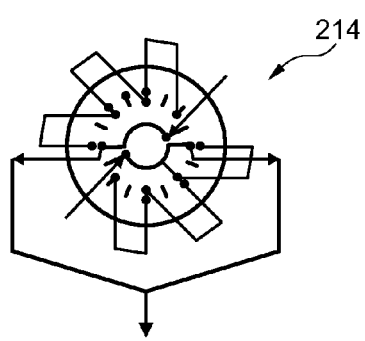
Fig. 10a　　　　　　　　Fig. 10b
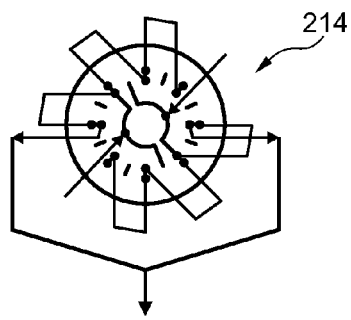
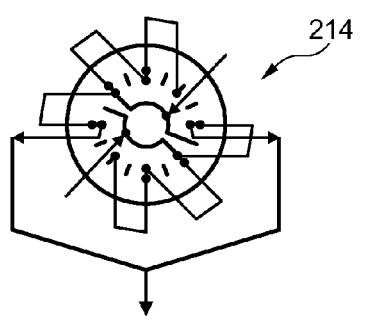
Fig. 10c　　　　　　　　Fig. 10d
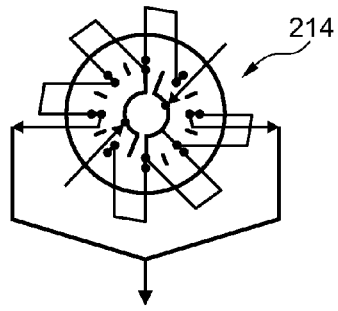
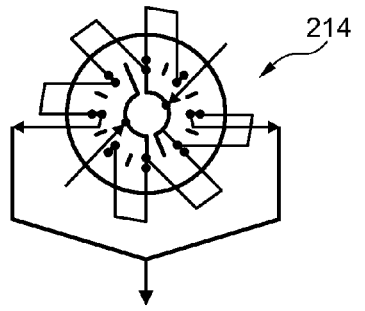
Fig. 10e　　　　　　　　Fig. 10f
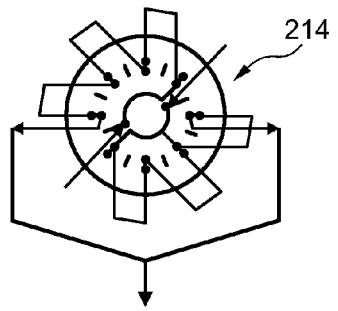
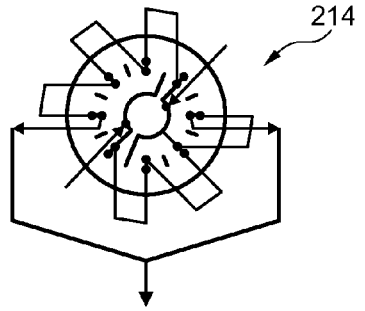
Fig. 10g　　　　　　　　Fig. 10h

FLUIDIC VALVE WITH SELECTIVELY SWITCHABLE STORAGE PATHS

The present application is a National Stage Application under 35 U.S.C. §371 and claims priority under 35 U.S.C. §121 from International Patent Application No. PCT/EP2012/062394 filed on Jun. 26, 2012. The entire disclosure of International Patent Application No. PCT/EP2012/062394 is specifically incorporated herein by reference.

BACKGROUND ART

The present invention relates to sample separation apparatus, a method for separating a fluidic sample and a respective computer program, as well as to a fluidic valve.

In liquid chromatography, a fluidic sample and a mobile phase may be pumped through conduits and columns in which separation of the sample takes place. The column may comprise a material which is capable of separating different components of the fluidic sample.

Two-dimensional separation of a fluidic sample is a separation technique in which a first separation procedure in a first separation unit is performed to separate a fluidic sample into a plurality of fractions, and in which a subsequent second separation procedure in a second separation unit is performed to further separate the plurality of fractions.

Typically in two-dimensional chromatography, a first fraction of a fluidic sample is separated in the second separation unit while the output of the first separation unit is stored in a storage path which may then be subsequently coupled to the second separation unit for further separation.

The sample characteristics as well as the speed differences by which the mobile phases with the sample are driven through the first separation unit and the second separation unit may require an adaption of the storage path of the sample separation apparatus. The change of a storage path is performed by removing a present storage path and fluidically coupling a desired storage path with the sample separation apparatus in order to obtain the desired storage characteristics (e.g. storage volumes).

After fluidically coupling the desired storage path with the sample separation apparatus, tightness of the coupling has to be checked.

DISCLOSURE

There may be a need for providing an improved sample separation apparatus with improved efficiency.

According to an exemplary embodiment of first aspects of the herein disclosed subject matter, a sample separation apparatus for separating a fluidic sample is provided, the sample separation apparatus comprising a first separation unit for separating the fluidic sample; a first fluid drive configured for generating a fluid flow for conducting the fluidic sample to be separated through the first separation unit; a second separation unit, arranged downstream of the first separation unit, for further separating the fluidic sample after treatment by the first separation unit; a second fluid drive configured for generating a fluid flow for conducting the fluidic sample or at least parts thereof, after treatment by the first separation unit, through the second separation unit; a fluidic valve having a first inlet fluidically coupled to one of the first fluid drive and the second fluid drive; the fluidic valve having a second inlet fluidically coupled to the other of the first fluid drive and the second fluid drive; the fluidic valve comprising at least two different sets of storage paths, wherein each set of storage paths comprises a first storage path; and wherein the first storage path of a first set of said at least two sets of storage paths has a first volume and the first storage path of a second set of said at least two sets of storage paths has a second volume different from the first volume; the fluidic valve being configured for selectively switching one set of said least two sets of storage paths to the first inlet and the second inlet.

According to an embodiment, the fluidic valve further comprising a first outlet and a second outlet, the fluidic valve being selectively switchable into a first state and a second state. According to an embodiment, the first outlet and the second outlet are distinct outlets. In other embodiments, the first outlet and the second outlet are provided by a same, single outlet which optionally is fluidically coupled to the second separation unit. According to an embodiment, the first outlet and/or the second outlet are external outlets, i.e. they are configured to be fluidically coupled with an external flow path. According to another embodiment, the first outlet and/or the second outlet are internal outlets, i.e. they are fluidically coupled to a further component of the fluidic valve. According to an embodiment, the first outlet and the second outlet are distinct outlets. According to a further embodiment, the first outlet and the second outlet are provided by a single common outlet.

According to an embodiment, the fluidic valve comprising at least one of the following features: (i) in the first state the first inlet is fluidically coupled to the first outlet and the second inlet is fluidically coupled to the second outlet, wherein optionally the first inlet is fluidically coupled to the first outlet via the first storage path of the first set; and (ii) in the second state in the first inlet is fluidically coupled to the second outlet and the second inlet is fluidically coupled to the first outlet, wherein optionally the second inlet is fluidically coupled to the first outlet via the first storage path of the first set.

According to an embodiment, the sample separation apparatus a, further comprises the following feature: the fluidic valve being selectively switchable into the first state and into the second state for each of at least one set of said at least two sets of storage paths.

According to an embodiment, the sample separation apparatus further comprises the following feature: for each of at least one first set of said at least two sets of storage paths, the first outlet and the second outlet are both fluidically coupled to the second separation unit; wherein optionally, first outlet and the second outlet are both permanently fluidically coupled to the second separation unit.

According to an embodiment, the fluidic valve further comprises: a third outlet, wherein optionally the third outlet is a waste outlet bypassing the second separation unit.

According to an embodiment, the fluidic valve further comprises at least one of the following groups of features: (i) for at least one of said sets, the fluidic valve is switchable into a third state in which the second inlet is fluidically coupled, via the first storage path of the set, to at least one of the first outlet the second outlet and in which the first inlet is fluidically coupled to the third outlet, optionally via the second storage path of the set; (ii) for at least one of said sets, the fluidic valve is switchable into a fourth state in which the first inlet is fluidically coupled, via the first storage path of the set, to at least one of the first outlet and the second outlet and the second inlet is fluidically coupled to the third outlet, optionally via the second storage path of the set.

According to an embodiment, at least one set of said at least two different sets of storage paths comprises a second storage path; wherein for each of the at least one set, if the set is switched to the first inlet and the second inlet, in the first state the first inlet is fluidically coupled to the first storage path of the set and the second inlet is fluidically coupled to the second storage path of the set; and wherein for each of the at least one set, if the set is switched to the first inlet and the second inlet, in the second state the first inlet is fluidically coupled to the second storage path of the selected set and the second inlet is fluidically coupled to the first storage path of the selected set.

The sample separation apparatus further comprises: the fluidic valve being configured such that of the selected set of storage paths, which is switched to the first inlet and to the second inlet, the first storage path is fluidically coupled to the first outlet and the second storage path is fluidically coupled to the second outlet in both, the first state and the second state.

According to an embodiment, the sample separation apparatus further comprises at least one of the following features: a first base fluid path moveable to a first position corresponding to the first state and moveable to a second position corresponding to the second state of the fluidic valve; the first base fluid path fluidically coupling the first inlet and the first outlet in the first state; the first base fluid path fluidically coupling the first inlet and the second outlet in the second state; a second base fluid path moveable to a first position corresponding to the first state and moveable to a second position corresponding to the second state of the fluidic valve; the second base fluid path fluidically coupling the second inlet and the second outlet in the first state; the second base fluid path fluidically coupling the second inlet and the first outlet in the second state.

According to an embodiment, the first base fluid path comprises: a first port region fluidically coupled to the first inlet; a second port region moveable to be fluidically coupled to the first outlet in the first state and moveable to be fluidically closed in the second state; and a third port region moveable to be fluidically coupled to the second outlet in the second state and moveable to be closed in the first state, wherein the first port region, the second port region and the third port region of the first base fluid path are fluidically coupled to each other.

According to an embodiment, the second base fluid path comprises: a first port region fluidically coupled to the second inlet; a second port region moveable to be fluidically coupled to the second outlet in the first state and moveable to be fluidically closed in the second state; and a third port region moveable to be fluidically coupled to the first outlet in the second state and moveable to be closed in the first state; wherein the first port region, the second port region and the third port region of the second base fluid path are fluidically coupled to each other.

According to an embodiment, the sample separation apparatus further comprises at least one of the following features: the first base fluid path and/or the second base fluid path being a groove in a moveable member; the first base fluid path and the second base fluid path are provided in a single moveable member.

According to an embodiment, the first storage path of the second set of storage paths includes at least one of the following features: the second volume is larger than the first volume; the first storage path of the second set of storage paths includes at least part of the first storage path of the first set of storage paths.

According to an embodiment, if the first storage paths of the at least two sets are ordered so as to have ascending volumes, a first storage path of a next set, which has a volume that is larger than the volume of the first storage path of each of the preceding sets, includes the first storage path of the preceding set and an additional storage path element; wherein optionally the first storage path of the first set, of which the first storage path has the smallest volume, includes only a single storage path element.

According to an embodiment, the fluidic valve further comprises: a moveable coupling element; the moveable coupling element being moveable into at least two coupling positions of which each coupling position corresponds to a selection of one of the at least two sets of storage paths.

According to an embodiment, each additional first storage path of the at least two sets has a first port and a second port. According to a further embodiment, the fluidic valve further comprises: the moveable coupling element having at least one coupling fluid path; wherein in each coupling position the at least one coupling fluid path fluidically couples the storage paths elements of all preceding sets and the additional storage path element of the set corresponding to the coupling position via their first ports and their second ports, thereby providing the first storage path of the set of storage paths corresponding to the coupling position.

According to a further embodiment, one of the first coupling fluid path and the second coupling fluid path fluidically couples the first storage path of the set of storage paths corresponding to the coupling position to an outlet port; wherein optionally the at least one coupling fluid path is a groove in the moveable coupling element.

According to an embodiment, the movement of the moveable coupling element defines a path of motion of the at least one coupling fluid path. According to a further embodiment, the sample separation apparatus further comprising at least one of the following features: the first port and the second port of each first storage path element is located in a position overlapping the path of motion of the at least one coupling fluid path; the extent of the coupling fluid path in a direction along its path of motion is larger than the distance between the ports, to be coupled by the coupling fluid path, along the path of motion, wherein optionally of a first port and a second port to be coupled by the coupling fluid path at least a part of the first port is in line with the second port along the path of motion; the extent of the coupling fluid path perpendicular to the path of motion is larger than the distance, perpendicular to the path of motion, between the ports to be coupled by the coupling fluid path, wherein optionally of a first port and a second port to be coupled by the coupling fluid path at least a part of the first port is in line with the second port perpendicular to the path of motion.

According to an embodiment, at least one of the first base fluid path and the second base fluid path is provided in the moveable coupling element.

According to an embodiment, the extent of a coupling fluid path along the path of motion of the coupling fluid path is at least the distance along the path of motion between the ports to be coupled by the coupling fluid path plus the larger one of i) the distance along the path of motion between the first position and the second position of the first base fluid path and ii) the distance along the path of motion between the first position and the second position of the second base fluid path.

According to an embodiment, the at least one coupling fluid path comprises a first coupling fluid path and a second coupling fluid path different from the first coupling fluid path; in the first position of the first base fluid path a first port and a second port are coupled by the first coupling fluid path, and in the second position of the first base fluid path the first port and the second port are coupled by the second coupling fluid path.

According to an embodiment, the sample separation apparatus further comprises at least one of the following features: the first base fluid path is provided in a first switching element, the first switching element being moveable with regard to the moveable coupling element in order to switch one port of two end ports of the first storage path of the selected set into fluid communication with the first base fluid path or out of fluid communication with the first base fluid path; the second base fluid path is provided in a second switching element, the second switching element being moveable with regard to the moveable coupling element in order to switch one port of two end ports of the first storage path of the selected set into fluid communication with the second base fluid path or out of fluid communication with the second base fluid path; wherein optionally the second switching element is the first switching element; wherein optionally the sample separation apparatus comprises an actuator for driving the first switching element; and wherein optionally the first switching element comprises a stop face configured to be driveable, by the actuator, into contact with a corresponding stop face on the moveable coupling element, the moveable coupling element thereby being drivable by the first switching element upon further driving of the first switching element.

According to an embodiment, the sample separation apparatus further comprises at least one of the following features: the moveable coupling element is rotatable and is moveable into the at least two coupling positions by rotation of the moveable coupling element; wherein optionally the sample separation apparatus comprises the further features that the rotation of the moveable coupling element defines a circumferential direction and a radial direction perpendicular to the circumferential direction and that the at least one coupling fluid path comprises a circumferential groove section; wherein optionally sample separation apparatus comprises the further features that the at least one coupling fluid path comprises a radial groove extending in a radial direction. According to a further embodiment, the moveable coupling element is linearly moveable coupling element being moveable into the at least two coupling positions along a linear axis.

According to an embodiment, the sample separation apparatus further comprises at least one of the following features: the sample separation apparatus comprises at least one actuator for controllably moving moveable elements; the sample separation apparatus comprising a flow coupler having two fluid inlet terminals and a fluid outlet terminal in fluid communication with one another, the fluid outlet terminal being fluidically coupled or coupleable to the second separation unit; wherein optionally the flow coupler is configured as one of the group consisting of a fluidic T-piece, and a fluidic Y-piece; wherein the first separation unit is arranged between the first fluid drive and one of the first inlet and the second inlet of the fluidic valve which the fluidic valve fluidically couples with the first fluid drive; wherein the second separation unit is directly fluidically coupled to the fluid outlet terminal of the flow coupler; wherein the fluidic valve is switchable so that pressure conditions in the first separation unit and in the second separation unit remain constant before and after switching; the sample separation apparatus comprises a detector for detecting the separated fluidic sample and being arranged downstream of the second separation unit; the sample separation apparatus comprises a sample injector for injecting the fluidic sample into a mobile phase and being arranged between the first fluid drive and the first separation unit; wherein the first fluid drive is operable with a first flow rate being smaller than a second flow rate according to which the second fluid drive is operable; wherein optionally the second flow rate is at least five times, particularly is at least ten times, more particularly is at least fifty times, of the first flow rate; wherein the fluidic valve is switchable for performing the separation of the fluidic sample so that the first fluid drive and the second fluid drive are in fluid communication with one another via the flow coupler in at least some of the switching states of the fluidic valve. According to an embodiment, the flow coupler is internal to the fluidic valve. For example, the flow coupler and the fluidic valve may be arranged in a common housing. In such an embodiment, the first outlet and the second outlet are internal outlets which are fluidically coupled to the flow coupler. According to other embodiments, the flow coupler is external to the fluidic valve. For example, according to an embodiment, the first outlet and the second outlet of the fluidic valve are external outlets to which an external flow path, e.g. an external flow coupler, is coupleable.

According to an embodiment, the sample separation apparatus comprises a control device configured for: controlling the first separation unit to execute a primary separation sequence for separating the fluidic sample into a plurality of fractions; controlling the second separation unit to execute at least one secondary separation sequence for further separating at least a part of the plurality of fractions; wherein optionally at least one of the primary separation sequence and the at least one secondary separation sequence relates to a chromatographic gradient run. The first separation unit is also referred to as separation unit of a first dimension and the second separation unit is also referred to as separation unit of a second dimension.

According to an embodiment, the sample separation apparatus comprises at least one of the following: the first separation unit and the second separation unit are configured so as to execute the respective sample separation in accordance with different separation criteria, particularly in accordance with at least partially orthogonal separation criteria, more particularly having different selectivity patterns to the relevant sample components;

The sample separation apparatus according to any one of the preceding claims, comprising at least one of the following features: the sample separation apparatus comprises a control device configured for controlling operation of at least one of the group consisting of the first fluid drive, the second fluid drive and the fluidic valve; at least one of the first separation unit and the second separation unit is configured for performing a separation in accordance with one of the group consisting of liquid chromatography, supercritical-fluid chromatography, capillary electrochromatography, electrophoresis and gas chromatography; the sample separation apparatus is configured as a two-dimensional liquid chromatography sample separation apparatus, particularly being a comprehensive two-dimensional liquid chromatography apparatus; the sample separation apparatus is configured to analyze at least one physical, chemical and/or biological parameter of at least one compound of the fluidic sample; the sample separation apparatus comprises at least one of the group consisting of a chromatography device, a liquid chromatography device, an HPLC device, a gas chromatography device, a capillary electrochromatography device, an electrophoresis device, a capillary electrophoresis device, a gel electrophoresis device, and a mass spectroscopy device; the sample separation apparatus is configured for generating a fluid flow for conducting the fluidic sample with a high pressure; the sample separation apparatus is configured for generating a fluid flow for conducting the fluidic sample with a pressure of at least 100 bar, particularly of at least 500 bar, more particularly of at least 1000 bar; the sample separation apparatus is configured to conduct a liquid fluid; the sample separation apparatus is configured as a microfluidic device; the sample separation apparatus is configured as a nanofluidic device; at least one of the group consisting of the first separation unit and the second separation unit is configured for retaining at least a part of components of the fluidic sample and for allowing other components of the fluidic sample to pass; at least one of the group consisting of the first separation unit and the second separation unit comprises a separation column; at least one of the group consisting of the first separation unit and the second separation unit comprises a chromatographic column; at least a part of at least one of the group consisting of the first separation unit and the second separation unit is filled with a separating material.

According to an exemplary embodiment of a second aspect of the herein disclosed subject matter, a method of separating a fluidic sample is provided, the method comprising: conducting the fluidic sample to be separated through a first separation unit by a fluid flow generated by a first fluid drive; conducting, after treatment by the first separation unit, at least one fraction of the fluidic sample through a second separation unit downstream of the first separation unit assisted by fluid flow generated by a second fluid drive; for performing the separation of the fluidic sample, switching a fluidic valve having a first inlet and a second inlet fluidically coupled to the first fluid drive and the second fluid drive; selectively switching one set of at least two different sets of storage paths to the first inlet and to the second inlet.

According to an embodiment, in a method as disclosed herein the fluidic valve is configured in accordance with one or more embodiments of the herein disclosed subject matter. According to a further embodiment, in a method as disclosed herein a sample separation apparatus in accordance with one or more embodiments of the herein disclosed subject matter is used for performing separation of the fluidic sample.

According to an exemplary embodiment of a third aspect of the herein disclosed subject matter, a software program or product is provided, preferably stored on a data carrier, the software program or product being adapted for executing a method to one or more embodiments of the herein disclosed subject matter, when run on a data processing system such as a computer.

According to an exemplary embodiment of a fourth aspect of the herein disclosed subject matter, a fluidic valve is provided, the fluidic valve having a first inlet and a second inlet; the fluidic valve comprising at least two different sets of storage paths; the fluidic valve being configured for selectively switching one set of said least two sets of storage paths to the first inlet and to the second inlet.

According to an embodiment, the fluidic valve is configured in accordance with one or more embodiments of the herein disclosed subject matter. According to a further embodiment, the fluidic valve is employed in and/or mounted to a sample separation apparatus according to one or more embodiments of the herein disclosed subject matter.

In accordance with an embodiment, the pressure in the mobile phase might range from 2-200 MPa (20 to 2000 bar), in particular 10-150 MPa (100 to 1500 bar), and more particular 50-120 MPa (500 to 1200 bar).

In the context of this application, the term "fluidic sample" may particularly denote any liquid and/or gaseous medium, optionally including also solid particles, which is to be analyzed. Such a fluidic sample may comprise a plurality of fractions of molecules or particles which shall be separated, for instance biomolecules such as proteins. Since separation of a fluidic sample into fractions involves a certain separation criterion (such as mass, volume, chemical properties, etc.) according to which a separation is carried out, each separated fraction may be further separated by another separation criterion (such as mass, volume, chemical properties, etc.), thereby splitting up or separating a separate fraction into a plurality of sub-fractions.

In the context of this application, the term "fraction" may particularly denote such a group of molecules or particles of a fluidic sample which have a certain property (such as mass, volume, chemical properties, etc.) in common according to which the separation has been carried out. However, molecules or particles relating to one fraction can still have some degree of heterogeneity, i.e. can be further separated in accordance with another separation criterion.

In the context of this application, the term "sub-fractions" may particularly denote individual groups of molecules or particles all relating to a certain fraction which still differ from one another regarding a certain property (such as mass, volume, chemical properties, etc.). Hence, applying another separation criterion for the second separation as compared to the separation criterion for the first separation allows these groups to be further separated from one another by applying the other separation criterion, thereby obtaining the further separated sub-fractions.

In the context of this application, the terms "inlet" and "outlet" may particularly indicate that in a general flow direction of fluid through the device, the fluid will be conducted via at least one of the first inlet and the second inlet towards one of the first outlet and the second outlet. However, this terminology does not exclude (at least temporarily) other flow directions, for instance a fluid flow from one of the fluid inlets to the other one of the fluid inlets via for example, a flow combiner, for instance for pressure equilibration purposes. In a similar way this terminology does also not exclude that, in a certain operating mode, there may also be temporarily a back flow from at least one of the fluid outlets to at least one of the fluid inlets.

In the context of this application, the term "downstream" may particularly denote that a fluidic member located downstream compared to another fluidic member will only be brought in interaction with a fluidic sample after interaction with the other fluidic member (hence being arranged upstream). Therefore, the terms "downstream" and "upstream" relate to a flowing direction of the fluidic sample.

In the context of this application, the term "sample separation apparatus" may particularly denote any apparatus which is capable of separating different fractions of a fluidic sample by applying a certain separation technique. Particularly, two separation units may be provided in such a sample separation apparatus when being configured for a two-dimensional separation. This means that the sample is first separated in accordance with a first separation criterion (in the first dimension), and is subsequently separated in accordance with a second, different, separation criterion (in the second dimension). The difference in the separation criterion may provide different selectivity patterns for the separation in the first and the second dimension.

The term "separation unit" may particularly denote a fluidic member through which a fluidic sample is transferred and which is configured so that, upon conducting the fluidic sample through the separation unit, the fluidic sample will be separated into different groups of molecules or particles (called fractions or sub-fractions, respectively). An example for a separation unit is a liquid chromatography column which is capable of trapping and selectively releasing different fractions of the fluidic sample.

In the context of this application, the term "fluid drive" may particularly denote any kind of pump which is configured for delivery of a fluidic mobile phase and/or a fluidic sample along a fluidic path. A corresponding liquid supply system may comprise two fluid drives, such as the first fluid drive can be configured to conduct a mobile phase (solvent composition) as well as a fluidic sample, through the first separation unit, whereas the second fluid drive can be configured for conducting a further mobile phase (solvent composition) as well as a fluidic sample or its fractions after treatment by the first separation unit through the second separation unit.

In the context of this application, the term "flow coupler" may particularly denote a fluidic component which is capable of unifying flow components from two fluid inlet terminals into one common fluid outlet terminal. For example, the outlets of a fluidic valve as disclosed herein may be fluidically coupled to the fluid inlet terminals of the flow coupler. By the flow coupler, a bifurcated flow path may be provided in which two streams of fluids flow towards a bifurcation point are unified to flow together through the fluid outlet terminal. At a bifurcation point where the fluid inlet terminals and the fluid outlet terminal are fluidically connected, fluid may flow from any source terminal to any destination terminal depending on actual pressure conditions, thereby allowing for some sort of equilibration. The flow coupler may act as a flow combiner for combining flow streams from the two fluid inlet terminals further flowing to the fluid outlet terminal. The flow coupler may provide for a permanent (or for a selective) fluid communication between the respective fluid terminals and connected conduits, thereby allowing for a pressure equilibration between these conduits. In certain embodiments, the flow coupler may also act as a flow splitter.

In the context of this application, the term "fluidic valve" may particularly denote a fluidic component which has fluidic interfaces such as inlets, outlets and internal ports, wherein upon switching the fluidic valve selective ones of the fluidic interfaces may be selectively coupled to one another so as to allow fluid to flow along a corresponding fluidic path, or may be decoupled from one another, thereby disabling fluid communication.

According to an exemplary embodiment of the invention, a two-dimensional sample separation system is provided which comprises a fluidic valve with at least two different sets of storage paths, wherein the fluidic valve is configured for selectively switching one set of storage paths to the first inlet and the second inlet of the fluidic valve depending of the requirements of a specific sample separation to be performed. A corresponding sample separation control scheme may be applied by embodiments of the herein disclosed subject matter to a two-dimensional sample separation architecture in which the fluidic sample is firstly separated into fractions by applying a first separation criterion, and subsequently each separated fraction may be further separated into subsections by applying a different second separation criterion.

When the sample separation system is a liquid chromatography system such as a HPLC, the first separation unit and/or the second separation unit may be a liquid chromatography column.

In an embodiment, the first separation unit is arranged between (particularly downstream of) the first fluid drive and (particularly upstream of) the corresponding fluidic interface (e.g. the corresponding inlet) of the fluidic valve. Therefore, the first fluid drive may be fluidically coupled to its assigned fluidic interface of the fluidic valve indirectly via the first fluid separation unit. Hence, the first fluid drive may be operative to conduct the fluidic sample through the first separation unit. Before the separation by the first separation unit, the first fluid drive may add a mobile phase (i.e. a solvent composition which may be varied over time by the first fluid drive and an assigned proportioning valve) to the fluidic sample. For example, it is possible that the first fluid drive varies a solvent composition over time so as to carry out a gradient run in the first separation unit. Thereby, the fluidic sample may be separated into multiple fluidic components at an outlet of the first separation unit by liquid chromatography.

In an embodiment, the second separation unit for further separating the fluidic sample after treatment (usually separation) by the first separation unit may be arranged downstream of the first separation unit and downstream of the fluidic valve so as to further separate the already separated fractions of the fluidic sample into sub-fractions. For this purpose, it may be advantageous that the second separation unit operates in accordance with another separation technique or even separation criterion as compared to the first separation unit.

In an embodiment, the sample separation apparatus comprises a flow coupler having two fluid inlet terminals and a fluid outlet terminal in fluid communication with one another, the fluid outlet terminal being fluidically connectable to the second separation unit.

In an embodiment, the second separation unit is arranged at the fluid outlet terminal of a flow coupler. Therefore, the fluidic sample separated or treated by the first separating unit as well as a solvent provided by the second fluid drive may be mixed at the bifurcation point of the flow coupler and may together be coupled into the second separation unit.

In an embodiment, the flow coupler is configured as a fluidic T-piece, a fluidic Y-piece, or a fluidic X-piece. In case of a fluidic T piece and a fluidic Y piece, two flow streams are combined at one bifurcation point into a single outlet path. In the case of a fluidic X piece, there may be one further fluid conduit. This further fluid conduit can be a second fluid outlet conduit or a third fluid inlet conduit. Other kinds of flow couplers are possible as well.

In an embodiment, the flow coupler comprises at least one check valve preventing fluid from flowing in a reversed direction in at least one of the terminals. This may eliminate undesired back flow of fluid in an unwanted direction.

In an embodiment, the fluidic valve comprises a first valve member and a second valve member being movable, particularly being rotatable, relative to one another to thereby adjust different operation modes of the sample separation apparatus. Particularly, when such a fluidic valve is configured as a rotary valve, it may be constituted by a stator and a rotor both having fluid conduits, wherein in an embodiment, the first valve member is the rotor and the second valve member is the stator. By rotating the rotor relative to the stator, a desired operation mode may be adjusted. Other embodiments include a first valve member and a second valve member which are linearly moveable with respect to each other. According to an embodiment, the first valve member is or comprises a moveable member and/or a moveable coupling element according to one or more embodiments of the herein disclosed subject matter.

In an embodiment, the fluidic valve is configured to be switchable to a first state in which the fluidic interface fluidically coupled to the first fluid drive is in fluid communication via the fluidic valve with the fluidic interface fluidically coupled to one of the fluid inlet terminals of the flow coupler, and in which the fluidic interface fluidically coupled to the second fluid drive is in fluid communication via the fluidic valve with the flow coupler fluidic interface fluidically coupled to the other one of the fluid inlet terminals. Thus according to an embodiment, in the first state, it may always be ensured that the two fluid drives are in fluid communication.

It is also possible that the fluidic valve is configured to be switchable, starting from the first state, to a second state in which the fluidic interface fluidically coupled to the first fluid drive is in fluid communication via the fluidic valve with the fluidic interface fluidically coupled to the other one of the flow coupler fluid inlet terminals, and in which the fluidic interface fluidically coupled to the second fluid drive is in fluid communication via the fluidic valve with the fluidic interface fluidically coupled to the one of the flow coupler fluid inlet terminals. Since also in the second operation mode fluid communication between the two fluid drives remains enabled, pressure drops or ripples are also suppressed in this state. Only during the extremely short time interval for switching the switching valve between the first state and the second state (for instance several milliseconds), the two fluid drives may be fluidically decoupled from one another. However, since this switching time may be as short as 20 ms or even shorter, this will not have a noteworthy impact on the continuous pressure characteristics.

In an embodiment, the first valve member comprises one or more ports forming the fluidic interfaces, and the second valve member comprise one or more grooves for fluidically coupling different fluidic interfaces depending on a switching state of the fluidic valve. Thus, a fluid flow may be enabled between an inlet port, a certain one of the grooves and an outlet port. By moving (e.g. rotating) the grooves along the arrangement of the ports, different fluid communication and paths can be adjusted, while disabling flow along other paths.

In an embodiment, at least one of the first fluid drive and the second fluid drive is a binary fluid pump. The term "binary fluid pump" may particularly relate to a configuration in which the fluid pump pumps a corresponding mobile phase with a composition of two components. For example, when such a solvent composition is used for a chromatography gradient run, the ratio between water as a first solvent and acetonitrile (ACN) as a second solvent may be adjusted so as to trap and later release an individual fraction on a chromatography column. However, other pumps such as a quaternary pump may be used as well.

In an embodiment, the fluidic valve is switchable so that pressure conditions in the first separation unit and in the second separation unit remain basically constant upon switching. This may significantly improve the performance of the separation, particularly of the chromatographic separation. The arrangement of the fluidic interfaces of the fluidic valve in relation to the fluid drives and the separation units may allow to achieve these conditions. Without pressure ripples, there will also be no artifacts and no deteriorating impact on the fluid separating material in the separating units.

In an embodiment, the sample separation apparatus comprises a detector for detecting the separated fluidic sample and being arranged in the fluid outlet terminal downstream of the second separation unit. Thus, a detector for detecting the individual fractions and sub-fractions may be arranged downstream of the second separating unit. Such a detector may operate on the basis of an electromagnetic radiation detection principle. For example, an electromagnetic radiation source may be provided which irradiates the sample passing through a flow cell with primary electromagnetic radiation (such as optical light or ultraviolet light). In response to this irradiation with primary electromagnetic radiation, there will be an interaction of this electromagnetic radiation with the fluidic sample so that resulting secondary electromagnetic radiation may be detected being indicative of the concentration and kind of fluidic fractions.

In an embodiment, the sample separation apparatus comprises a sample injector for injecting the fluidic sample into a mobile phase and being arranged between the first fluid drive and the first separation unit. In such a sample injector, an injection needle may suck a metered amount of fluidic sample into a connected loop. After driving and inserting such an injection needle in a corresponding seat and upon switching a fluid injection valve, the fluidic sample may be injected into the path between first fluid drive and first separating unit. Upon such a switching operation, a mobile phase transported by the fluid drive and constituted by a solvent composition may be mixed with the fluidic sample.

In an embodiment, the first fluid drive is operable with a first flow rate (pumped fluid volume per time interval) which may be smaller than a second flow rate (pumped fluid volume per time interval) according to which the second fluid drive is operable. Due to the two-dimensional separation procedure, the amount of solvent per time interval pumped by the first fluid drive may be significantly smaller than another solvent composition pumped by the second fluid drive. Also a pressure (for instance a pressure value in a range between 50 bar and 400 bar, for instance 200 bar) applied by the first fluid drive may be smaller than a pressure (for instance a pressure value in a range between 500 bar and 1500 bar, for instance 800 bar) applied by the second fluid drive.

In an embodiment, the second flow rate is at least five times, particularly is at least ten times, more particularly is at least fifty times, of the first flow rate. For example, a flow rate of the second fluid drive may be in a range between about 1 ml/min and about 10 ml/min, whereas a flow rate of the first fluid drive may be in a range between about 10 μl/min and about 500 μl/min.

In an embodiment, the sample separation apparatus comprises a control device configured for controlling one or more of the fluidic devices thereof to keep the pressure at a certain position or in a certain segment of the fluidic path at a predefined value. Hence, the control unit may be a microprocessor or the like controlling a pumping performance of the first supply unit, a pumping performance of the second supply unit and/or a switching characteristic of the fluidic valve may be configured so that the flow rate of the fluid is allowed to vary over time. In accordance to this, the parameter kept constant over the measurement may be the pressure.

In an embodiment, the sample separation apparatus comprises a control device configured for controlling the first separation unit to execute a primary separation sequence for separating the fluidic sample into a plurality of fractions, and controlling the second separation unit to execute at least one secondary separation sequence for further separating at least a part of the separated plurality of fractions into a plurality of sub-fractions. In the context of this application, the term "primary separation sequence" may particularly denote a procedure according to which a fluidic sample is to be separated in the first separation unit. This may include a plurality of steps to be carried out subsequently. In a preferred embodiment, the primary separation sequence is a gradient run by which the fluidic sample is separated in the first separation unit by changing a ratio of two solvents gradually, thereby selectively trapping and later releasing individual fractions of the fluidic sample on the first separation unit. In the context of this application, the term "at least one second separation sequence" may particularly denote one or more sequences having a similar or the same characteristic as the first sequence but which are to be executed by the second separation unit. According to an embodiment, the fluidic sample is split or separated into the various fractions during execution of the primary separation sequence, whereas the secondary separation sequence(s) chop the separated fractions into further subsections by applying another, at least partially different separation criterion. For example, with a long-lasting primary separation sequence, the sample can be separated into a plurality of fractions by a first separation criteria (for instance the mass). In the subsequent, at least partially orthogonal secondary separation sequences, each fraction separated during the primary separation sequence can be further separated into a plurality of sub-fractions (particularly in accordance with another separating criterion such as an affinity to a certain stationary phase). The result of such a separation can be displayed in a two-dimensional coordinate system, both axis plotting the corresponding retention volume.

In an embodiment, the first separation unit and/or the second separation unit may be configured for performing a separation in accordance with liquid chromatography, supercritical-fluid chromatography, capillary electrochromatography, electrophoresis and gas chromatography. However, alternative separating technologies may be applied as well.

The sample separation apparatus may be configured as a fluid separation system for separating components of the sample. When a mobile phase including a fluidic sample passes through the fluidic device, for instance by applying a high pressure, the interaction between a filling of the column and the fluidic sample may allow for separating different components of the sample, as performed in a liquid chromatography device.

The sample separation apparatus may be implemented in different technical environments, like a sensor device, a test device, a device for chemical, biological and/or pharmaceutical analysis, a capillary electrophoresis device, a capillary electrochromatography device, a liquid chromatography device, a gas chromatography device, or an electronic measurement device. Particularly, the fluidic device may be a High Performance Liquid Chromatography device (HPLC) device by which different fractions of an analyte may be separated, examined and/or analyzed.

The separation unit may be a chromatographic column for separating components of the fluidic sample. Therefore, exemplary embodiments may be particularly implemented in the context of a liquid chromatography apparatus.

The sample separation apparatus may be configured to conduct the mobile phase through the system with a high pressure, particularly of at least 600 bar, more particularly of at least 1200 bar.

The sample separation apparatus may be configured as a microfluidic device. The term "microfluidic device" may particularly denote a fluidic device as described herein which allows to convey fluid through microchannels having a dimension in the order of magnitude of less than 500 µm, particularly less than 200 µm, more particularly less than 100 µm or less than 50 µm or less. The sample separation apparatus may also be configured as a nanofluidic device. The term "nanofluidic device" may particularly denote a fluidic device as described herein which allows to convey fluid through nanochannels having even smaller dimensions than the microchannels.

In the above there has been described and in the following there will be described exemplary embodiments of the subject matter disclosed herein with reference to a sample separation apparatus, a fluidic valve, a method of separating a fluidic sample and respective software program or product. It has to be pointed out that of course any combination of features relating to different aspects of the herein disclosed subject matter is also possible. In particular, some embodiments have been or will be described with reference to apparatus type features whereas other embodiments have been or will be described with reference to method type features. However, a person skilled in the art will gather from the above and the following description that, unless otherwise notified, in addition to any combination of features belonging to one aspect also any combination between features relating to different aspects or embodiments, for example even between features of the apparatus type embodiments and features of the method type embodiments is considered to be disclosed with this application.

According to embodiments of the herein disclosed subject matter, apparatus type features are adapted for providing the functionality of one or more of the embodiments of the method type features and/or for providing the functionality as required by one or more of the embodiments of the method type features.

According to further embodiments of the herein disclosed subject matter, method type features are adapted for providing the functionality of one or more of the embodiments of the apparatus type features and/or for providing the functionality as required by one or more of the embodiments of the apparatus type features.

The aspects and embodiments defined above and further aspects and embodiments of the present invention are apparent from the examples to be described herein after and are explained with reference to the drawings but to which the invention is not limited.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

FIG. 5a and FIG. 5b show a fluidic valve in accordance with embodiments of the herein disclosed subject matter.

FIG. 6a and FIG. 6b show a further fluidic valve in accordance with embodiments of the herein disclosed subject matter.

FIG. 7a and FIG. 7b show a further fluidic valve in accordance with embodiments of the herein disclosed subject matter.

FIG. 8a and FIG. 8b show a further fluidic valve according to embodiments of the herein disclosed subject matter.

FIG. 10a to FIG. 10h show the fluidic valve of FIG. 6a and FIG. 6b in the possible switching positions.

Figure 1:
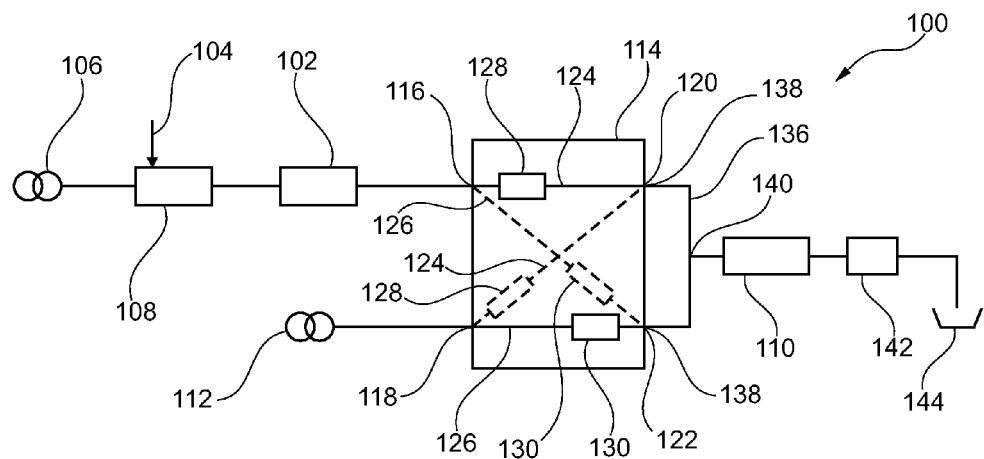
FIG. 1 illustrates a sample separation apparatus according to embodiments of the herein disclosed subject matter.

The illustrations in the drawings are schematic.

FIG. 1 illustrates a sample separation apparatus 100 according to embodiments of the herein disclosed subject matter.

In accordance with an embodiment, the sample separation apparatus comprises a first separation unit 102, e.g. a first chromatographic column, for separating a fluidic sample 104. Further, in accordance with an embodiment the sample separation apparatus 100 comprises a first fluid drive 106 configured for generating a fluid flow for conducting the fluidic sample 104 to be separated through the first separation unit 102.

In accordance with an embodiment, the sample separation apparatus 100 comprises an injection device 108 for injecting the fluidic sample 104 into the fluid flow. For example, according to an embodiment the sample separation apparatus 100 is a liquid chromatography apparatus and the fluid flow into which the fluidic sample 104 is injected by the injection device 108, is a mobile phase.

According to an embodiment, the sample separation apparatus 100 comprises a second separation unit 110, e.g. a second chromatographic column. The second separation unit 110 is arranged downstream of the first separation unit 102 for further separating the fluidic sample 104 after treatment of the first separation unit 102. Further in accordance with an embodiment, the sample separation apparatus comprises a second fluid drive 112 configured for generating a fluid flow for conducting the fluidic sample 104 or at least parts thereof, after treatment by the first separation unit 102, through the second separation unit 110.

In accordance with an embodiment, the first fluid drive 106 and the second fluid drive 112 are pump devices including at least one pumping unit for driving a mobile phase.

According to an embodiment, the sample separating apparatus 100 comprises a fluidic valve 114 having a first inlet 116 fluidically coupled to one of the first fluid drive 106 and the second fluid drive 112. According to an embodiment, the first inlet 116 of the fluidic valve 114 is fluidically coupled to the first fluid drive 106, as shown in FIG. 1.

According to an embodiment, the fluidic valve 114 has a second inlet 118 fluidically coupled to the other of the first fluid drive 106 and the second fluid drive 112. For example, according to an embodiment, the second inlet 118 of the fluidic valve 114 is fluidically coupled to the second fluid drive 112, as shown in FIG. 1.

According to an embodiment, the sample separation apparatus 100 comprises a first outlet 120 and a second outlet 122. In accordance with an embodiment, the fluidic valve 114 is switchable into a first state, in which the first inlet 116 is fluidically coupled to the first outlet 120, e.g. by a flow path 124 and the second inlet 118 is fluidically coupled to the second outlet 122, e.g. by a flow path 126. In accordance with an embodiment, the first state of the fluidic valve 114 is indicated by solid lines used for the flow paths 124, 126.

According to an embodiment, the fluidic valve 114 is switchable into a second state, in which the first inlet 116 is fluidically coupled to the second outlet 122, e.g. by the second flow path 126 and the second inlet 118 is fluidically coupled to the first outlet 120, e.g. by the first flow path 124. In FIG. 1, the second state is indicated by dashed lines used for the flow paths 124, 126.

According to an exemplary method of operation of the sample separation apparatus 100, the method comprises injecting the fluidic sample 104 into the mobile phase driven by the first fluid drive 106, and driving the fluidic sample 104 and the mobile phase through the first separation unit 102, thereby separating the fluidic sample 104 in different components of the fluidic sample 104.

Now an exemplary operation of the fluidic valve 114 according to embodiments of the herein disclosed subject matter is described in greater detail. In accordance with an embodiment, the fluidic valve 114 comprises a first storage path 128, into which the separated components from the first separation unit 102 are driven if the fluidic valve 114 is in the first state. According to an embodiment, the first storage path 128 forms part of the first flow path 124, as shown in FIG. 1.

According to an embodiment, the first storage path 128 is switched to the second input 118 if the separated components which shall be further investigated by the second separation unit 110, are located in the first storage path 128. This corresponds to the second state of the fluidic valve 114. Hence, in the second state of the fluidic valve 114 the first storage path 128 is fluidically coupled between the second inlet 118 and the first outlet 120. Hence, since the second inlet 118 is fluidically coupled with the second fluid drive 112, the separated components in the first storage path 128 are drivable by the second fluid drive 112 through the first outlet 120 and through the second separation unit 110.

According to an embodiment, the fluidic valve 114 comprises a second storage path 130 which is fluidically coupled between the first inlet 116 and the second outlet 122 in the second state of the fluidic valve 114. According to an embodiment, the second storage path 130 forms part of the second flow path 126, as shown in FIG. 1. It is noted that the location of the storage paths 128, 130 with regard to the flow paths 124, 126 as shown in FIG. 1 is not limiting but has been chosen for clarity purposes of FIG. 1. While however of course the flow paths 124, 126 with its their storage paths 128, 130 may be configured differently e.g. in length, volume and location of the storage path, in another embodiment, the flow paths 124, 126 are configured identically or symmetrically.

Having again regard to FIG. 1, while the separated components contained in the first storage path 128 are driven through the second separation device 110, further separated components of the fluidic sample 104 are provided by the first separation unit 102 and are driven, by the first fluid drive 106, into the second storage path 130. According to an embodiment, driving the separated components contained in the first storage path 128 through the second separation device 110 may occur during a first time interval and driving the further separated components into the second storage path 130 may occur during a second time interval, wherein the first time interval and the second time interval may be identical regarding duration and the location in time, or, according to other embodiments the first time interval and the second time interval may be different in at least one parameter.

Once the further components of the fluidic sample 104 are located in the second storage path 130 and the separation of the different components in the first storage path 128 is performed to an extent that the switching of the fluidic valve 114 from the second state back into the first state does not adversely affect the separation of the different components from the first storage path 128 in the second separation unit 110, the fluidic valve 114 is switched back to the first state. If desired, the method can be repeated.

In some applications it is desirable to adapt the size of the first storage path 128 and/or the second storage path 130 to the operating conditions of the sample separation apparatus 100 and/or to the fluidic sample 104 that is analyzed by the sample separation apparatus 100. For example, according to an embodiment it is desirable to change at least one of the volumes of the first storage path 128 and the second storage path 130 in order to operate the sample separation apparatus 100 more efficiently or in order to provide more flexibility to the adjustment of the operating parameters of the sample separation apparatus 100 to a particular fluidic sample 104, just to name some examples.

According to an embodiment, the sample separation apparatus 100 comprises a flow coupler 136 having two fluid inlet terminals 138 and a fluid outlet terminal 140 in fluid communication with one another. The fluid outlet terminal 140 of the flow coupler 136 is fluidically coupled to the second separation unit 110. In particular, in accordance with an embodiment the second separation unit 110 is directly fluidically coupled to the fluid outlet terminal 140 of the flow coupler 136. Hence, according to an embodiment, the first outlet 120 and the second outlet 122 are both fluidically coupled to the second separation unit 110. For example, according to an embodiment the first outlet 120 and the second outlet 122 are both permanently fluidically coupled to the second separation unit 110, as shown in FIG. 1.

Further in accordance with an embodiment, the sample separation apparatus 100 comprises a detector 142 for detecting the separated fluidic sample and being arranged downstream the second separation unit 110. In accordance with an embodiment, a waste collection site 144 is provided downstream the detector 142 for collecting the separated and detected components of the fluidic sample 104.

In accordance with an embodiment, the fluidic valve 114 is switchable for performing the separation of the fluidic sample 104 so that the first fluid drive 106 and the second fluid drive 112 are in fluid communication with one another via the flow coupler 136 in at least some of the switching states, e.g. in the first state as well as in the second state of the fluidic valve 114.

According to a more general embodiment in the first state the first inlet 116 is fluidically coupled to the first storage path 128 of the selected set and the second inlet 118 is fluidically coupled to the second storage path 130 of the selected set. Further in the more general embodiment, in the second state the first inlet 116 is fluidically coupled to the second storage path 130 of the selected set and the second inlet 118 is fluidically coupled to the first storage path 128 of the selected set. For example, the fluidic valve 114 shown in FIG. 1 is in accordance with this general embodiment.

In accordance with the further more general embodiment, the fluidic valve 114 is configured such that of the selected set of storage paths, which is switched to the first inlet 116 and to the second inlet 118, the first storage path 128 is fluidically coupled to the first outlet 120 and the second storage path 130 is fluidically coupled to the second outlet 122 in both, the first state and the second state.

Figure 2:
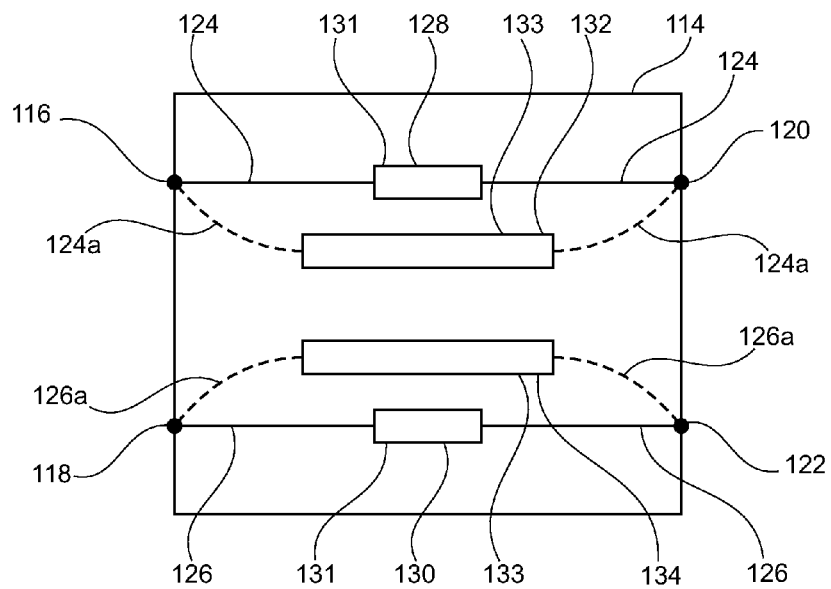
FIG. 2 illustrates the fluidic valve of the sample separation apparatus of FIG. 1 in greater detail.

FIG. 2 illustrates the fluidic valve 114 of the sample separation apparatus 100 of FIG. 1 in greater detail.

In accordance with an embodiment, the fluidic valve 114 comprises at least two different sets of storage paths, e.g. two sets of storage paths as shown in FIG. 2. A first set 131 of storage paths includes the first storage path 128 and the second storage path 130 which have already been shown in FIG. 1 and discussed with regard to FIG. 1. A second set 133 of storage paths includes a first storage path 132 and a second storage path 134.

In accordance with an embodiment, the first storage path 128 of the first set 131 has a first volume and a first storage path 132 of the second set 133 has a second volume different from the first volume. For example, according to an embodiment the second volume is higher than the first volume. In accordance with an embodiment, the fluidic valve 114 is configured for selectively switching one set of the at least two sets 131, 133 of storage paths to the first inlet 116 and to the second inlet 118. Herein, it should be understood that selectively switching one set of storage paths to the first inlet 116 and to the second inlet 118 does not necessarily mean that one of the first storage paths and the second storage path of the selected set is fixedly switched to the first inlet 116 and the other of the first and second storage path is fixedly switched to the second inlet 118 without changing the association of storage paths 128, 130 and inlets 116, 118. Rather, in accordance with an embodiment, after having selectively switched one set of the at least two sets of storage paths to the first inlet 116 and to the second inlet 118, the fluidic valve 114 is also switchable into the first state in which the first storage path 128, 132 of the selected set is fluidically coupled with the first inlet 116 and the second storage path 130, 134 of the selected set is switched to the second inlet 118. Further, the fluidic valve 114 further comprises the second state in which the first storage path 128, 132 of the selected set is fluidically coupled to the second inlet 118 and the second storage path 130, 134 of the selected set is fluidically coupled to the first inlet 116 (the second state is not shown in FIG. 2 for the sake of clarity). For example, in FIG. 2 the first set 131 is switched to the first inlet 116 and the second inlet 118, indicated by the solid lines representing the flow paths 124, 126. Hence, the solid lines in FIG. 2 represent the first set 131 of storage paths being switched to the inlets 116, 118 and further correspond to the first state of the fluidic valve 114.

In accordance with an embodiment, the second set 133 of storage paths may be switched to the inlets 116, 118. The dashed lines 124a, 126a representing respective flow paths indicate that the second set 133 is not selected, i.e. the first flow path 132 and the second flow path 134 of the second set 133 is not fluidically coupled to the inlets 116, 118 in the depicted state of the valve 114. It should be understood that the flow paths 124a, 126a in the configuration shown in FIG. 2 correspond to the first state of the valve 114. Also for the second set 133 the second state of the valve 114 is not shown for the sake of clarity of FIG. 2.

By providing a fluidic valve 114 according to embodiments of the herein disclosed subject matter, the volume of the first storage path can selectively be changed by selectively switching a respective set 131, 133 of storage paths to the first inlet 116 and to the second inlet 118. Changing the volume of the storage path that is coupled to the first inlet 116 and to the second inlet 118 has the advantage that no longer a manual mounting of another storage path to the fluidic valve is necessary and hence for example a testing of the tightness of the fluidic connection between the fluidic valve 114 and the manually mounted storage path can be omitted. This may improve the efficiency of the use of the fluidic valve 114 and the use of the respective sample separation apparatus 100, in particular if a sequence of measurements requires a change of the volume of the respective storage path.

It should be understood, that in accordance with an embodiment the volume of the second storage path 130 of the first set 131 has a volume different from the second storage path 134 of the second set 133. Hence, in an embodiment the volume of both the first storage path and the second storage path can be changed by selectively switching a respective set 131, 133 of storage paths to the first inlet 116 and the second inlet 118. In other embodiments, where the set of storage paths includes only a single storage path, namely the first storage path 128, 132, only a single storage path is switched to the first inlet 116 and to the second inlet 118, wherein it should be understood that the first storage path 128, 132 is either switched to the first inlet 116 in the first state or to the second inlet 118 in the second state.

According to a further embodiment, the fluidic valve 114 is switchable into the first state or into the second state for at least one of the at least two sets 131, 133 of storage paths. For example, as described above with regard to FIG. 2 the fluidic valve 114 is switchable into the first state and into the second state for each of the sets 131, 133 of storage paths. According to other embodiments, only part of the at least two sets of storage paths provides switchability into the first state and into the second state. These sets of storage paths may be referred to as sets of a first type. However, in such a case there may be a third state of the fluidic valve, such that for example for at least one set of the first type the fluidic valve is switchable into the first state and into the second state and for at least one other set of storage paths, the fluidic valve is switchable into the first state and into the third state or, in still another embodiment into the second state and into the third state. In this context, the third state may be a third state as described with regard to embodiments of the herein disclosed subject matter. The sets which are switchable into the third state may be referred to as a set of a second type.

According to an embodiment, for each of the at least one set of the first type, the first outlet and the second outlet are both fluidically coupled to the second separation unit, e.g. by means of the flow coupler 136 described with regard to FIG. 1. According to another embodiment, for at least one set of the first type, the first outlet 120 and the second outlet 122 are not both fluidically coupled to the second separation unit 110. For example, in accordance with an embodiment, for such a set of the first type one of the outlets may be fluidically coupled directly to a waste collection site, e.g. the waste collection site 144 (not shown in FIG. 2).

Figure 3:
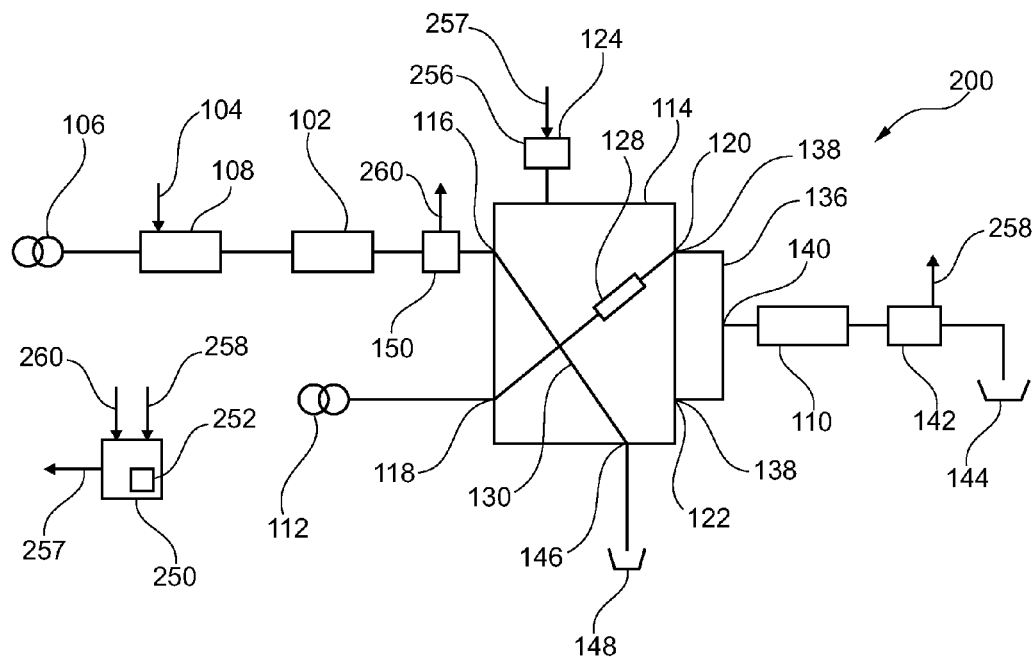
FIG. 3 illustrates a sample separation apparatus according to embodiments of the herein disclosed subject matter.

FIG. 3 illustrates a sample separation apparatus 200 according to embodiments of the herein disclosed subject matter.

The sample separation apparatus 200 comprises all features and/or the functionality of the sample separation apparatus 100 described with regards to FIGS. 1 and 2. Hence, the description of the respective features, which are denoted by the same reference signs, is not repeated here. According to other embodiments, the sample separation apparatus 200 may comprise only part of the features and/or the functionality of the sample separation apparatus 100 described with regards to FIGS. 1 and 2.

According to a further embodiment of the herein disclosed subject matter, the sample separation apparatus 200 comprises a third outlet 146 which in accordance with an embodiment is a waste outlet bypassing the second separation unit 110, as shown in FIG. 3. In accordance with an embodiment, the waste outlet 146 is fluidically coupled to a waste collection site 148. While according to an embodiment the waste collection site 148 and the waste collection site 144 are different entities, as shown in FIG. 3, in other embodiments the waste collection site 148 and the waste collection site 144 are identical (i.e. they are formed by the same entity).

According to an embodiment, for at least one set of storage paths, which may be referred to as being of the second type, the fluidic valve is switchable into a third state, in which the second inlet 118 is fluidically coupled to at least one of the first outlet 120 and the second outlet 122 via the first storage path 128 and in which the first inlet 116 is fluidically coupled to the third outlet 146, as shown in FIG. 3.

In accordance with an embodiment, the third outlet 146 may be used to remove part of the components of the fluidic sample 104 from the flow path to the second separation unit 110. In turn, this may referred to as cutting out part of the components separated by the first separation unit 102 and transfer the cutted components to the second separation unit 110. Since this "cutting" operation relates to cutting a heart, e.g. specifically interesting portion, of the components of the fluidic sample 104, the cutting operation is also referred to as "heart cutting". In order to perform the heart cutting, a further detector 150 may optionally be provided between the first separation unit 102 and the fluidic valve 114. The detector 150 may be adapted to allow to determine which components of the fluidic sample 104 are going into the fluidic valve 114. Upon detecting a desired portion of the components of the fluidic sample, the fluidic valve 114 in an embodiment is controlled in accordance with detection signals generated by detector 150. In other words, according to an embodiment the operation of the fluidic valve 114 is controlled, by means of the detector 150, so as to transfer a desired portion of the components of the fluidic sample 104, which portion is detected by the detector 150, to the second separation unit 110 by respectively operating the fluidic valve 114 according to embodiments of the herein disclosed subject matter. The detector 150 may also be referred to as "second detector" according to embodiments of the herein disclosed subject matter.

According to an embodiment, a controller 250 is provided, the controller 250 controlling operation of the fluidic valve 114. For example, according to an embodiment, the controller 250 comprises a data processing system 252 for executing a computer program adapted to execute a method according to one or more embodiments of the herein disclosed subject matter. According to an embodiment, the sample separation apparatus 200 comprises an actuator 256 for switching the fluidic valve 114 in accordance with embodiments of the herein disclosed subject matter. In particular, the actuator 256 may be adapted to perform at least one of the following: selectively switch one set of said least two sets of storage paths to the first inlet 116 and the second inlet 118; switch the fluidic valve 114 between the first state and the second state; switch the fluidic valve 114 between the first state and the third state; switch the fluidic valve 114 between the second state and the third state; switch the fluidic valve 114 between the first state and the fourth state (described below); switch the fluidic valve 114 between the second state and the fourth state; switch the fluidic valve 114 between the third state and the fourth state. For controlling the actuator 256, the controller 250 is in an embodiment adapted to provide a control signal 257 to the actuator 256. Further, the controller 250 may be adapted for receiving sensor signals 258, 260 from the first detector 142 and or from the second detector 150, respectively.

Figure 4:
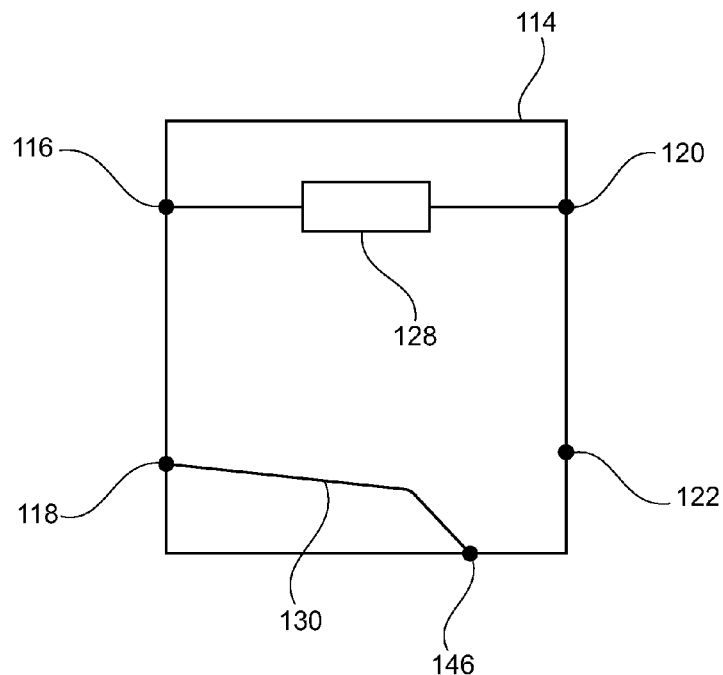
FIG. 4 shows the fluidic valve of the sample separation apparatus of FIG. 3 in a fourth state according to embodiments of the herein disclosed subject matter.

FIG. 4 shows the fluidic valve 114 of the sample separation apparatus 200 of FIG. 3 in a fourth state according to embodiments of the herein disclosed subject matter. In accordance with an embodiment, the fluidic valve 114 is further switchable into the fourth state.

According to an embodiment, in the fourth state the first storage path 128 is fluidically coupled to the first inlet 116. For example, according to an embodiment, in the fourth state the first inlet 116 is fluidically coupled to at least one of the first outlet and the second outlet via the first storage path 128 and the second inlet 118 is fluidically coupled to the third outlet 146, as shown in FIG. 4. In accordance with an embodiment, in the third state and the fourth state only the first storage path is switched to at least one of the first outlet 120 and the second outlet 122, for example to the first outlet 120 as shown in FIG. 3 and FIG. 4. In accordance with an embodiment the second storage path 130 is fluidically coupled to the third outlet in both, the third state and the second state. In other embodiments, the volume of the second storage path of the set of the second type is reduced to a minimum.

According to an embodiment, in the fourth state the first storage path 128 is fluidically coupled to the first inlet 116 and to the third outlet 146 (not shown in FIG. 4). According to a further embodiment, in the fourth state the second storage path 130 is coupled to the second inlet 118 and, optionally to the first outlet 120 (not shown in FIG. 4).

Generally herein, according to an embodiment, instead of coupling one of the first storage path 128 and the second storage path 130 to the first outlet 120, one of the first storage path 128 and the second storage path 130 may be fluidically coupled to the second outlet 122.

In the following not all details of the fluidic valves illustrated in the drawings have been referred to with a reference sign in order to improve clarity of the drawings. It should be noted that of course that features shown in a particular drawing, e.g. FIG. 5a, may be (and in some instances are) also present in other drawings, in particular FIG. 5b or FIG. 6a to FIG. 8b unless otherwise noted.

FIG. 5a shows the first state of a fluidic valve 114 in accordance with embodiments of the herein disclosed subject matter. FIG. 5b shows the second state of the fluidic valve 114 in accordance with embodiments of the herein disclosed subject matter.

The fluidic valve 114 comprises a first base fluid path 152 movable to a first position, shown in FIG. 5a, wherein the first position corresponds to the first state of the fluidic valve 114. The first base fluid path 152 fluidically couples the first inlet 116 and the first outlet 120 in the first state. Further in accordance with an embodiment, the fluidic valve 114 comprises a second base fluid path 154 movable to a first position corresponding to the first state of the fluidic valve 114. The second base fluid path 154 fluidically couples the second inlet 118 and the second outlet 122 in the first state. In accordance with an embodiment, the first base fluid path 152 is moveable to a second position, shown in FIG. 5b, wherein the second position corresponds to the second state of the fluidic valve 114. According to an embodiment, the first base fluid path 152 fluidically couples the first inlet 116 and the second outlet 122 in the second state. In accordance with a further embodiment, the second base fluid path 154 is movable to a second position corresponding to the second state, shown in FIG. 5b, of the fluidic valve. According to an embodiment, the second base fluid path 154 fluidically couples the second inlet 118 and the first outlet 120 in the second state as shown in FIG. 5b. The first outlet 120 and the second outlet 122 are fluidically coupled with a flow coupler 136 which may be configured according to one or more embodiments of the herein disclosed subject matter.

In accordance with an embodiment, the first base fluid path 152 comprises a first port region 156 fluidically coupled to the first inlet 116 in both, the first state and the second state. According to an embodiment, the first port region 156 has the shape of a segment of a circle, as shown in FIG. 5a and FIG. 5b. The extent of the segment is indicated by the bracket at 153. According to an embodiment, the first port region 156 is permanently fluidically coupled to the first inlet 116 irrespective the state or the coupling position of the fluidic valve 114. According to a further embodiment, the first base fluid path 152 comprises a second port region 158 movable to be fluidically coupled to the first outlet 120 in the first state and movable to be fluidically closed in the second state. In accordance with an embodiment, the first base fluid path 152 comprises a third port region 160 movable to be fluidically coupled to the second outlet 122 in the second state and movable to be closed in the first state.

In accordance with an embodiment, the fluidical coupling of the port regions 158, 160 to an outlet 120, 122 is effected by coupling corresponding port regions provided on valve members which are movable with respect to each other. For example, according to an embodiment the first base fluid path 156 is provided on a first valve member 162 whereas a corresponding coupling port 164 is provided on a second valve member (not shown in FIG. 5a and FIG. 5b for the sake of clarity). Hence, fluidic coupling of the first base fluid path 152 with an outlet 120, 122 is effected by moving the first valve member 162 and the second valve member with respect to each other until the respective port region 158, 160 of the first base fluid path 152 overlaps the corresponding coupling port 164 which is fluidically connected to the respective outlet 120, 122. Likewise, a port region 158, 160 of the first base fluid path 152 may be closed by moving the first valve member 162 with regard to the second valve member (i.e. with regard to the coupling ports 164) into a position in which the respective port region 158, 160 to be closed is not aligned with the corresponding coupling port 164.

According to an embodiment, the first port region 156, the second port region 158 and the third port region 160 of the first base fluid path 152 are fluidically coupled to each other, as shown in FIGS. 5a and 5b.

According to other embodiments the first port region 156, the second port region 158 and the third port region 160 may be fluidically coupled to each other to provide one or more functions according to embodiments of the herein disclosed subject matter.

According to an embodiment, the second base fluid path 154 is configured similar or identical to the first base fluid path. However in contrast to the first base fluid path 152, the second base fluid path 154 is adapted to provide the functionality according to one or more embodiments of the second base fluid path according to the herein disclosed subject matter.

For example, according to an embodiment, the second base fluid path 154 comprises a first port region 166, the first port region 166 being fluidically coupled to the second inlet 118 in both, the first state and the second state. According to an embodiment, the first port region 166 has the shape of a segment of a circle, as shown in FIG. 5a and FIG. 5b. The extent of the segment is indicated by the bracket at 153. According to an embodiment, the first port region 166 of the second base fluid path is permanently fluidically coupled to the second inlet 118 irrespective the state or the coupling position of the fluidic valve 114, as shown in FIG. 5a and FIG. 5b as well as in FIGS. 9a to 9h. In accordance with a further embodiment, the second base fluid path 154 comprises a second port region 168 movable to be fluidically coupled to the second outlet 122 in the first state and movable to be fluidably closed in the second state. Further in accordance with an embodiment, the second base fluid path 154 comprises a third port region 170 movable to be fluidically coupled to the first outlet 120 in the second state and movable to be closed in the first state. In accordance with an embodiment the first port region 166, the second port region 168 and the third port region 170 of the second base fluid path 154 are fluidically coupled to each other, or, in another embodiment, are fluidically coupled to each other to provide the functionality according to embodiments of the herein disclosed subject matter. Similar to the first base fluid path 152, fluidically coupling the port regions 168, 170 of the second base fluid path 154 to an outlet 120, 122 may be effected by aligning the respective port region 168, 170 with a corresponding coupling port 164 so that the respective port region at least partially overlaps the corresponding coupling port 164.

According to a further embodiment, the first base fluid path 152 and the second base fluid path 154 are formed by a groove in the first valve member 162. However, the first base fluid path and/or the second base fluid path may be provided by any suitable means, for example a tubing. According to an embodiment, the first valve member 162 is a movable member.

Generally herein, a movable entity (such as the moveable member 162) refers to an entity which is movable with regard to the fluidic valve 114 as such. For example, in an embodiment the movable entity is movable with regard to the inlet ports 116, 118 and the outlet ports 120, 122.

According to an embodiment, the first base fluid path 152 and the second base fluid path 154 are provided in a single movable member, for example in the member 162. In accordance with an embodiment, each set of storage paths of the at least two sets includes a first storage path which has a volume different from the volume of the first storage path of the other sets of storage paths. According to an embodiment, four sets of storage paths are provided, as shown in FIG. 5a and FIG. 5b. Further in accordance with an embodiment, the first storage path of the second set of storage paths includes at least part of the first storage path of the first set of storage paths. In accordance with an embodiment, a first storage path of a particular set which has a volume that is larger than the volume of a first storage path of at least one other set, includes the volume of the at least one other set.

Figure 9A:
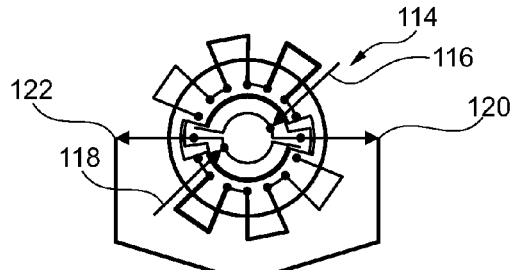
FIG. 9a to FIG. 9h show the fluidic valve of FIG. 5a and FIG. 5b in the possible switching positions.
Figure 9B:
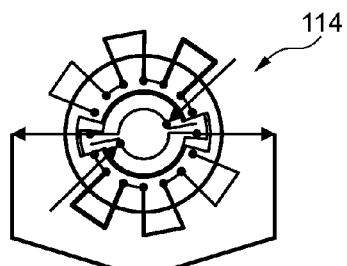

According to an embodiment, there may be provided dedicated storage path elements, e.g. storage path elements 172, 174, 176 of the first storage paths 178, 180, 182 of a first, second, and third set, respectively. As can be taken from FIG. 5a and FIG. 5b, also none of these dedicated storage path elements 172, 174, 176 may be switched to the first inlet 116 and the second inlet 118 (as shown in FIG. 9a and FIG. 9b below). In particular, it should be understood that any flow path represents some fluid storage capacity and hence is capable of forming a first storage path or a second storage path according to embodiments of the herein disclosed subject matter. For example, according to an embodiment, a connection fluid path connecting the storage path elements 172, 174, 176 with the respective inlet 116, 118 and the respective outlet 120, 122 forms a storage path element according to one or more embodiments of the herein disclosed subject matter. This storage path element in the form of the connection fluid path forms a zeroth set of storage paths. In accordance with an embodiment, the connection fluid path includes at least part of the first or second base fluid path 152, 154. Having again regard to the first state shown in FIG. 5a, the connection fluid path comprises a portion extending from the first inlet 116 to the additional storage path element 172 of the first set and a further portion extending from the storage path element 172 to the first outlet 120. The fluidic valve may also be switchable into a state in which the connection fluid path directly fluidically connects one of the first and second inlet with one of the first and second outlet, as shown in FIG. 9a and FIG. 9b. In accordance with an embodiment, the second port regions 158,168 of first and second base fluid path can be positioned overlapping the coupling port 164 of the first and second outlet 120, 122, respectively.

In accordance with an embodiment, each set of storage paths comprises a second storage path in addition to the first storage path of the set. In accordance with embodiments disclosed herein (see e.g. FIG. 7a and FIG. 7b), the first storage path and the second storage path of at least one set are different. According to other embodiments, the second storage path is configured similarly or identically to the corresponding first storage path of the set. For example, in accordance with an embodiment, a second storage path of the zeroth set of storage paths comprises a storage path element, i.e. a connection fluid path, which comprises at least part of the respective base fluid path. Further, a second storage path 186 of the first set of storage paths comprises a storage path element 188. Further, a second storage path 190 of the second set of storage paths comprises the storage path element 188 and an additional storage path element 192. According to a further embodiment, a second storage path 194 comprises the storage path elements 188, 192 of the second storage path of the first and the second sets as well as an additional storage path element 196.

In accordance with an embodiment, the zeroth set comprises the connection fluid paths, the first set comprises in addition the first storage path 178 and the second storage path 186, the second set comprises in addition the first storage path 180 and the second storage path 190, and the third set comprises in addition the first storage path 182 and the second storage path 194. In accordance with an embodiment, a single moveable coupling element 183 is configured for selecting both, the first storage path and the second storage path of the selected set of storage paths.

Having now regard to the first storage paths, the first storage path 178 of the first set comprises the connection fluid path and an additional storage path element, namely the storage path element 172. The first storage path 180 of the second set includes the storage path elements of the first set and the additional storage path element 174 of the second set. Further, the first storage path 182 of the third set includes the storage path elements of the second set as well as the additional storage path element 176. This results in the first storage path 180 of the first set, including the storage path element 172. Further, this results in the first storage path 180 of the second set, including the storage path elements 172, 174. Further, this results in the first storage path 182 of the third set which includes the storage path elements 172, 174, 176. It should be noted that in the configuration shown in FIG. 5a and FIG. 5b, the first set of storage paths including the first storage path 178 is selected out of the three sets of storage paths. According to an embodiment, the volume of the storage path elements 172, 174, 176 may be identical. According to other embodiments, the volume of the storage path elements 172, 174, 176 increases from the additional storage path element 172 of the first set to the additional storage path elements 174, 176 of the subsequent sets (if the sets are ordered so as to have ascending volumes of the first storage paths 178, 180, 182), as shown in FIG. 5a, FIG. 5b.

Hence, in accordance with an embodiment the numbering of the sets starts with zero and the ordering of sets is as follows (ascending volume of the first storage path): zeroth set with connection fluid path (including at least part of the first or the second base fluid path, depending on the state (FIG. 5a or FIG. 5b), first set with first storage path 178, second set with first storage path 180, third set with first storage path 182. Hence, if the fluidic valve 114 comprises n sets of storage paths with dedicated storage path elements, the total number of pairs of storage paths is n+1 since there is a flow path without a dedicated storage path element between one of the inlets and one of the outlets, as the flow path as such already forms a storage path in the sense of the herein disclosed subject matter. Having regard to FIG. 5a and FIG. 5b, hence the fluidic valve 114 comprises four sets of storage paths.

Hence, if the first storage paths 178, 180, 182 of the four sets of storage paths (including the zeroth set) are ordered to have ascending volumes, the first storage path 178, 180, 182 of a next set, which has a volume that is larger than the volume of the first storage path of each of the preceding sets includes the first storage path 178, 180 of the preceding set and an additional storage path element 172, 174, 176. Further it should be understood that the first storage path of the zeroth set, which has the smallest volume, includes only the connection fluid path. It should further be noted that the term "storage path element" as referred to herein may indeed comprise a single element or two or more elements. Hence, the term "storage path element" refers to the storage path portion which distinguishes the storage path of a particular set from the preceding sets of which the first storage path has a smaller volume than the first storage path of the particular set.

According to an embodiment, the fluidic valve 114 comprises a movable valve member in the form of a moveable coupling element 183 which is movable into at least two coupling positions of which each coupling position corresponds to a selection of one of the at least two sets of storage paths. The movable coupling element 183 comprises at least one coupling fluid path 184 for coupling the storage path elements 172, 174, 176, 188, 192, 196 and the first and the second base fluid path 152, 154 according to embodiments of the herein disclosed subject matter.

In accordance with an embodiment, each dedicated storage path element 172, 174, 176, 188, 192, 196 comprises two coupling ports 164 (i.e. a first coupling port and a second coupling port) by which the storage path element can be fluidically coupled to other ports or port regions according to embodiments of the herein disclosed subject matter. In particular, by means of the coupling ports 164, each storage path element 172, 174, 176, 188, 192, 196 may be fluidically coupled to a further storage path element 172, 174, 176, 188, 192, 196, to an inlet 116, 118 or to an outlet 120, 122, in accordance with embodiments of the herein disclosed subject matter.

Further, according to an embodiment each of the outlets 120, 122 is fluidically coupled to a respective coupling port 164.

According to an embodiment, coupling fluid paths 184 are provided on a moveable valve member (e.g. the moveable coupling element 183) whereas the coupling ports 164 are provided on a fixed valve member, e.g. as shown in FIG. 5a and FIG. 5b. According to an embodiment (not shown), coupling fluid paths 184 are provided on a fixed valve member whereas the coupling ports 164 are provided on a moveable valve member. However, it should be understood that only movability of components of the fluidic valve 114 with respect to each other is what is necessary to provide the functions according to one or more embodiments of the herein disclosed subject matter.

According to an embodiment, all coupling ports 164 of the outlets 120, 122 as well as of the storage path elements 172, 174, 176, 188, 192, 196 are arranged in a circle. This has the advantage, that the coupling ports 164 may be coupled by the coupling fluid path 184 if the coupling fluid paths have corresponding port regions which lie on the same circle. Hence, by rotating the movable coupling element 183 together with the at least one coupling fluid path 184, the dedicated storage path elements 172, 174, 176, 188, 192, 196 may be coupled to each other or some of these storage path elements may be coupled to each other in accordance with one or more embodiments of the herein disclosed subject matter. In particular, coupling of the storage path elements 152, 154, 172, 174, 176, 188, 192, 196 with the outlets 120, 122 may be performed so as to correspond to a selection of a respective set of storage paths, for example as shown in FIG. 5a and FIG. 5b so as to correspond to the selection of the first set of storage paths comprising the first storage path 178 and the second storage path 186. In accordance with an embodiment, the first base fluid path 152 and the second base fluid path 154 are movable so as to couple the first base fluid path 152 and the second base fluid path 154 to the selected storage path (first storage path in FIG. 5a and FIG. 5b) in accordance with one or more embodiments of the herein disclosed subject matter.

According to an embodiment, one or more coupling fluid paths 184 are each provided by a groove in the movable coupling element 183. However, in other embodiments, one or more coupling fluid paths 184 may each be provided by any other suitable means, for example by a tubing capable of fluidically coupling with coupling ports 164 in order to perform at least one function according to one or more embodiments of the herein disclosed subject matter.

According to an embodiment, the movement of the movable coupling element 183 defines a path of motion of the coupling fluid paths 184. Generally, the first port and the second port 164 of each dedicated storage path element 172, 174, 176, 188, 192, 196 is located in a position overlapping the path of motion of the coupling fluid paths 184. In accordance with an embodiment, the coupling fluid paths 184 lie on the same path of motion. According to another embodiment, the coupling fluid paths 184 do not lie on the same path of motion but have at least partially overlapping paths of motion, in order to provide the functionality according to one or more embodiments of the herein disclosed subject matter. For example, while in one embodiment it is preferred that the path of motion of the individual coupling fluid paths 184 are identical, these paths of motions may be different from each other for example, may have different radii. However, this requires larger coupling ports 164 in order to make sure that the respective coupling fluid paths 184 fluidically couple to the coupling ports 164 and hence to e.g. to the dedicated storage path elements 172, 174, 176, 188, 192, 196 or to the outputs 120, 122, according to one or more embodiments of the herein disclosed subject matter. However, in embodiments which are different from the general configuration described with regard to FIG. 5a and FIG. 5b, for example where the first base fluid path and/or the second base fluid path 152, 154 or at least the second and third port regions 158, 160, 168, 170 thereof are on a different level (i.e. in a different plane) than the coupling fluid path, also different configurations may provide the same functionality as described with regard to FIG. 5a, FIG. 5b. However, according to an embodiment, the second port region and the third port region 158, 160, 168, 170 of the first base fluid path 152 and the second base fluid path 154 are in the same plane of motion. That is, by appropriate movement of the movable coupling element 183 and the movable coupling member 162 either one of the second and third port regions of a base fluid path 152, 154 or a coupling fluid path 184 may be coupled with a respective coupling port 164. For example, according to an embodiment, all coupling ports 164 are located in a single plane. According to a further embodiment, this single plane is parallel to the plane of motion in which the motion of the movable coupling element 183 and/or the motion of the movable member 162 takes place.

According to an embodiment, the first base fluid path 152 and the second base fluid path 154 are provided in the same movable member 162. According to an embodiment, the movable coupling element 183 and the movable member 162 are both moveable and, optionally, are also moveable with respect to each other. According to an embodiment, the movable coupling element 183 and the movable member 162 are both rotatable. According to a further embodiment, one of the movable coupling element 183 and the movable member 162 have a radial protrusion and the other one of the movable coupling element 183 and the movable member 162 comprise a corresponding recess into which the protrusion extends. In accordance with an embodiment, the movable coupling element 183 and the movable member 162 have a limited movability with regard to each other. According to an embodiment, the limited movability of the movable coupling element 183 and the movable member 162 corresponds to the movability required for switching between the first state and the second state of the fluidic valve 114. According to an embodiment, one of the movable coupling element 183 and the movable member 162 is an entrainer for the other of the movable coupling element 183 and the movable member 162.

For example, according to an embodiment, the movable member 162 is an entrainer for the movable coupling element 183. According to an embodiment, to this end the movable member 162 comprises a protrusion 198 which extends into a corresponding recess 202 of the movable coupling element 183. Since the protrusion 198 of the movable member 162 engages the recess 202 of the movable coupling element 183, the movable member thereby forms an entrainer for the movable coupling element 183. In accordance with an embodiment, the recess 202 has a larger extent in circumferential direction then the extent of the protrusion 198 in circumferential direction. In other words, if the protrusion 198 engages a stop face of the recess 202, an opposite stop face of the recess 202 is spaced from the protrusion 198 by a predefined angle of rotation 204. According to an embodiment, this predefined angle of rotation 204 corresponds to the angle of rotation necessary for the movable member 162 to rotate for switching between the first state and the second state of the fluidic valve 114. Hence, according to an embodiment, a rotation of the movable coupling element 183 allows a selection of one set of storage paths out of the three sets of storage paths of the fluidic valve 114 while a rotation of the movable member 162 between the stop faces of the recess 202 corresponds to a switching between the first state and the second state for the selected set of storage paths.

For example, in accordance with embodiments of the herein disclosed subject matter, FIG. 5a shows the movable coupling element 183 in a rotational position where a first set of storage paths is selected, the first set of storage paths comprising the first storage path 178 and the second storage path 186, wherein in FIG. 5a the movable member 162 is in a position corresponding to the first state of the fluidic valve 114 for the selected first set and FIG. 5b corresponds to the second state of the fluidic valve 114 for the selected first set. Accordingly, the position of the movable coupling element 183 is the same in FIG. 5a and FIG. 5b, corresponding to the same selected set of storage paths (i.e. the first set of storage paths).

According to an embodiment, the movable member 162 comprises two protrusions, the protrusion 198 and a further protrusion 206, which is located in a corresponding recess 208 of the movable coupling element 183. The further protrusion 206 and the corresponding recess 208 are configured similarly or identically to the protrusion 198 and the recess 202 described above. Therefore, the detailed description thereof is not repeated here.

According to an embodiment, the third port region 160, 168 of the first base fluid path 152 and the second base fluid path 154 are located on the recess 198. Further according to an embodiment, the second port region 158, 170 of the first base fluid path 152 and the second base fluid path 154 are located on the further protrusion 206. In this way, the second and third port regions 158, 160, 168, 170 of the base fluid paths 152, 154 are located in the path of motion of the coupling fluid paths 184.

Further shown in FIG. 5b are the opposite stop faces 210 provided by the recess 202, 208 and the corresponding stop faces 212 on the protrusions 198, 206 of the movable member. Indicated at 256 in FIG. 5b is an actuator for driving the movable member 162. It should be understood that by the opposing stop faces 210, 212 of the movable coupling element 183 and the movable member 162 the movable coupling element 183 may be driven by the actuator 256 via the movable member 162. The actuator 256 may be any suitable actuator, for example a step motor.

With regard to FIG. 5a and FIG. 5b, an exemplary fluidic valve 114 has been described. While in FIG. 5a and FIG. 5b the first base fluid path 154 and the second base fluid path 156 are located on the same movable member 162, according to other embodiments this is not necessarily the case. For example, in accordance with an embodiment, the first base fluid path 154 may be provided on a first switching element and the second base fluid path 156 may be provided on a second switching element. While in the exemplary fluidic valve 114 of FIG. 5a and FIG. 5b the first switching element and the second switching element are implemented by the same single switching element in the form of the moveable member 162. According to other embodiments, the first switching element may be different from the second switching element. However, it should be understood that even by providing the first switching element which is different from the second switching element, the same functionality as described with regard to one or more embodiments of the herein disclosed subject matter may be obtained.

While for a fluidic valve according to embodiments of the herein disclosed subject matter a single actuator 256 is sufficient for operating the fluidic valve 114, according to other embodiments two separate actuators may be provided, one for driving the movable member 162 and one for driving the movable coupling element 183.

As illustrated with regard to FIG. 5a and FIG. 5b, according to an embodiment the movable coupling element is rotatable and is movable into at least two coupling positions by rotation of the movable coupling element 183. According to an embodiment, the rotation of the movable coupling element 183 defines a circumferential direction 216 and a radial direction perpendicular to the circumferential direction 216. In accordance with an embodiment, the coupling fluid paths 184 comprise a circumferential groove section, as shown in FIG. 5a, FIG. 5b.

However, it should be understood that according to other embodiments, the at least one coupling fluid path may comprise a radial groove extending in radial direction perpendicular to the circumferential direction 216, as shown in FIG. 6a and FIG. 6b.

FIG. 6a and FIG. 6b show a further fluidic valve 214 in accordance with embodiments of the herein disclosed subject matter. In FIG. 6a and FIG. 6b some features may be similar or identical to respective features described with regard to FIG. 5a and FIG. 5b. Such features are referred to with the same reference signs as in FIG. 5a and FIG. 5b or are not assigned with reference signs for the sake of clarity and the description of these features is not repeated here. Rather, with regard to FIG. 6a and FIG. 6b the differences between the fluidic valve 114 in FIG. 5a and FIG. 5b and the fluidic valve 214 in FIG. 6a and FIG. 6b are emphasized.

In particular, in accordance with an embodiment, the coupling fluid paths are radially extending fluid paths or at least comprise radially extending fluid paths. For example, according to an embodiment, the radially extending coupling fluid paths 284 are implemented by radial grooves extending in a radial direction perpendicular to the circumferential direction 216. For example, according to an embodiment, the extent of the coupling fluid path 284 perpendicular to the path of motion of the coupling fluid path 284 in circumferential direction 216 is larger than the minimum distance, perpendicular to the path of motion, between ports 218, 220 to be coupled by the coupling fluid paths 284. Hence, the coupling fluid paths 284 are positionable so as to overlap the ports 218, 220 to be coupled. According to a further embodiment, of a first port 218 and a second port 220 to be coupled by the coupling fluid paths 284, at least part of the first port 218 is in line with the second port 220 in a direction perpendicular to the path of motion, i.e., according to an embodiment perpendicular to the circumferential direction 216. In other words, according to an embodiment, at least part of the first port 218 is in line with the second port 220 in radial direction perpendicular to the circumferential direction 216, as shown in FIG. 6a and FIG. 6b. For example, according to an embodiment, the second port 220 is associated with a first storage path element 172 and the first port 218 which is coupleable therewith, is associated with a second storage path element 174, for example as shown in FIG. 6a and FIG. 6b. This provides for short coupling fluid paths 284. Hence, in comparison with FIG. 5a and FIG. 5b, while in FIG. 5a and in FIG. 5b the coupling ports 164 to be coupled are spaced in circumferential direction and are coupled/coupleable in circumferential direction, according to an embodiment shown in FIG. 6a and FIG. 6b the coupling ports to be coupled are spaced from each other in radial direction and are coupled/coupleable in radial direction.

According to an embodiment, the angular distance 222 between two radial coupling fluid paths 284 is the same as the angular distance 224 between the second port region 158 of the first base fluid path 152 and the third port region 170 of the second base fluid path 154, as shown in FIG. 6a. Hence and generally according to an embodiment, the coupling fluid paths 284 allow for coupling of respective dedicated storage path elements 172, 174, 176, 188, 192, 196 while at the same time allowing for switching between the first state (FIG. 6a) and the second state (FIG. 6b) of the fluidic valve 214. According to an embodiment, the angular distance between the second port region 158 of the first base fluid path 152 and the third port region 170 of the second base fluid path 154 is identical to the angular distance between the third port region 160 of the first base fluid path 152 and the second port region 168 of the second base fluid path 154. According to an embodiment, the angular distance 222 between two neighboring radial coupling fluid paths 284 is half the angular distance 226 between two neighboring pairs of coupling ports each pair of which is to be coupled with a radial coupling fluid path 284. This allows for an embodiment of the herein disclosed subject matter, according to which the base fluid paths 152, 154 are provided on the movable coupling element 183. Hence, in accordance with an embodiment, only a single movable member, namely the movable coupling element 183 is provided in the fluidic valve 214. The angular distances between the radial coupling fluid path 284 as described above allow for a switching of the fluidic valve 214 between the first state shown in FIG. 6a and the second state, shown in FIG. 6b by a rotation of the movable coupling element 183 by the angular distance 224 between the second port region 158 of the first base fluid path 152 and the third port region 170 of the second base fluid path 154. Moreover, a selection of one set of storage paths is performed by rotation of the movable coupling element 183 by an angular distance 226 corresponding to the angular distance between corresponding pairs of coupling ports 164 which are to be coupled with the radial coupling fluid path 284. However there is an angular region 228 which corresponds to three times the angular distance 222 wherein no radial coupling fluid path is provided. This angular range 228 is necessary to allow for decoupling of two circumferentially neighboring storage path elements, such as the storage path element 172 of the first set and the additional storage path element 174 of the second set. Hence, the angular range 228 free of radial coupling fluid paths 284 allows for a selective fluidic coupling of the dedicated storage path elements 172, 174, 176.

FIG. 7a and FIG. 7b show a further fluidic valve 314 in accordance with embodiments of the herein disclosed subject matter.

While the fluidic valve 314 provides two sets of storage paths including a first storage path 178 and a second storage path 186 of a first set and a first storage path 180 and a second storage path 190 of a second set, the fluidic valve 314 also comprises a third set of storage paths which however is not switchable between a first state and a second state as described with regard to one or more embodiments of the herein disclosed subject matter, but which is switchable between a third state and a fourth state as described with regard to one or more embodiments of the herein disclosed subject matter.

In accordance with an embodiment, the fluidic valve 314 comprises a third outlet 146, wherein in the third state the second inlet 118 is fluidically coupled to the second outlet 122 and in which the first inlet 116 is fluidically coupled to the third outlet 146. According to an embodiment shown in FIG. 7a, the first inlet 116 is directly fluidically coupled to the third outlet 146 by the first base fluid path. Hence, in the sense of embodiments of the herein disclosed subject matter, the first base fluid path 152 forms the first storage path of the third set of the fluidic valve 314. The fluidic valve 314 further comprises a closure element 232 to which the second storage path 190 is fluidically coupled in the third state and fourth state so as to close the second storage path 190. In this way flow back of sample fluid through the flow combiner 136 and through the first outlet 120 into the fluidic valve 314 can be avoided.

FIG. 7b shows the fluidic valve 314, with the third set of storage paths selected, in a fourth state. Hence, in accordance with an embodiment, the first inlet 116 is fluidically coupled with the second outlet 122 via the second storage path 194 of the third set.

FIG. 8a and FIG. 8b show a further fluidic valve 414 according to embodiments of the herein disclosed subject matter.

The fluidic valve 414 in FIG. 8a and FIG. 8b has, in accordance with an embodiment, circumferential coupling fluid paths 384. Moreover, the first base fluid path 152 and the second base fluid path 154 are both located on the same movable coupling element 183 on which the circumferential coupling fluid paths 384 are provided. In order to provide for a switching between a first state (shown in FIG. 8a) and the second state (FIG. 8b) according to embodiments of the herein disclosed subject matter, the coupling fluid paths 384 have an extent in circumferential direction which is the distance between the ports 218, 220 to be coupled by the coupling fluid path 384 plus the angular distance between the first position (corresponding to the first state) and the second position (corresponding to the second state) of the moveable coupling element. Hence, the coupling fluid path 384 comprises an additional portion 230 extending beyond one of the two ports 218, 220 to be coupled by the coupling fluid paths 384. This additional portion 230 allows for a switching between the first state (FIG. 8a) and the second state (FIG. 8b) without switching the selected set of storage path.

Compared to the fluidic valve 114 of FIG. 5a and FIG. 5b, the additional portion 230 of coupling fluid paths 384 allow the base fluid paths 152, 154 to be located on the same moveable coupling element on which the coupling fluid paths 384 are provided. Hence, the moveable member 162 of the fluidic valve 114 can be omitted. However, reducing the size of the additional portion 230 has the advantage that the dead volume is reduced and carry-over of samples between subsequent measurements can be avoided or at least reduced.

The remaining features of the fluidic valve 414 correspond to respective features of FIG. 5a and FIG. 5b, the detailed description of which is not repeated here.

Figure 9C:
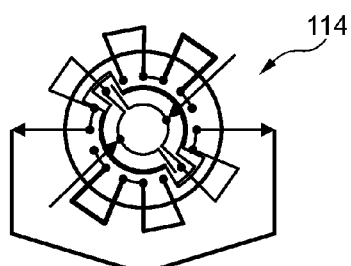
Figure 9D:
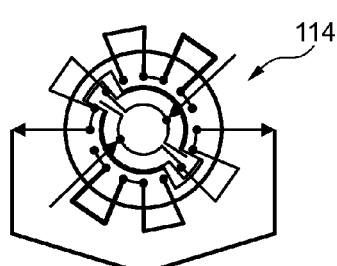
Figure 9E:
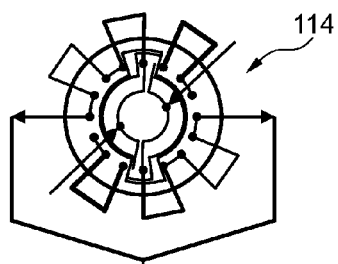
Figure 9F:
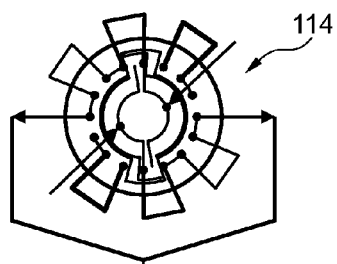
Figure 9G:
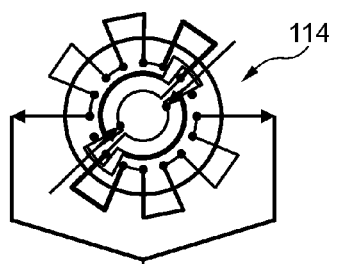
Figure 9H:
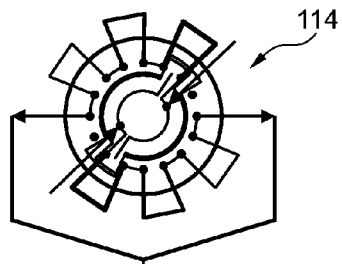

FIG. 9a to FIG. 9h show the fluidic valve 114 of FIG. 5a and FIG. 5b in the possible switching positions. Herein, the switching positions shown on the left hand side (FIG. 9a, 9c, 9e, 9g) correspond to the first state and the switching positions shown on the right hand side (FIG. 9b, 9d, 9f, 9h) correspond to the second state. Different pairs of Figures (shown in different "lines"), i.e. FIG. 9a, 9b; FIG. 9c, 9d; FIG. 9e, 9f; FIG. 9g, 9h correspond to different coupling positions, i.e. to different selected sets of storage paths. The individual elements in FIG. 9a to FIG. 9h are not labeled for the sake of clarity. However, the individual elements shown are the same as the individual elements shown and described in detail with regard to FIG. 5a and FIG. 5b.

In FIG. 9a and FIG. 9b show the valve 114 with none of the three sets of storage paths with dedicated storage path elements switched to the first inlet 116 and the second inlet 118 but with at least part of the first base fluid path 152 forming a storage path element of the zeroth set, and at least part of the second base fluid path 154 forming a storage path element of the zeroth set, in accordance with embodiments of the herein disclosed subject matter.

In FIG. 9c and FIG. 9d show the valve 114 with the first set of storage paths switched to the first inlet 116 and the second inlet 118. In particular, FIG. 9c and FIG. 9d correspond to FIG. 5a and FIG. 5b. In FIG. 9e and FIG. 9f show the valve 114 with the second set of storage paths switched to the first inlet 116 and the second inlet 118. In FIG. 9g and FIG. 9h show the valve 114 with the third set of storage paths switched to the first inlet 116 and the second inlet 118.

FIG. 10a to FIG. 10h show the fluidic valve 214 of FIG. 6a and FIG. 6b in the possible switching positions. Herein, the switching positions shown on the left hand side (FIG. 10a, 10c, 10e, 10g) correspond to the first state and the switching positions shown on the right hand side (FIG. 10b, 10d, 10f, 10h) correspond to the second state. The individual elements in FIG. 10a to FIG. 10h are not labeled for the sake of clarity. However, the individual elements shown are the same as the individual elements shown and described in detail with regard to FIG. 6a and FIG. 6b.

In FIG. 10a and FIG. 10b show the valve 214 with none of the three sets of storage paths with dedicated storage path elements switched to the first inlet 116 and the second inlet 118, in accordance with embodiments of the herein disclosed subject matter.

In FIG. 10c and FIG. 10d show the valve 214 with the first set of storage paths switched to the first inlet 116 and the second inlet 118. In particular, FIG. 10c and FIG. 10d correspond to FIG. 6a and FIG. 6b. In FIG. 10e and FIG. 10f show the valve 214 with the third set of storage paths switched to the first inlet 116 and the second inlet 118. In FIG. 10g and FIG. 10h show the valve 214 with the fourth set of storage paths switched to the first inlet 116 and the second inlet 118.

FIG. 11a to FIG. 11h show the fluidic valve 314 of FIG. 7a and FIG. 7b in the possible switching positions. Herein, the switching positions shown in FIG. 11a, 11c, 11e correspond to the first state and the switching positions shown in FIG. 11b, 11d, 11f correspond to the second state. Moreover, the switching position shown in FIG. 11g corresponds to the third state and the switching position shown in FIG. 11h corresponds to the fourth state. The individual elements in FIG. 11a to FIG. 11h are not labeled for the sake of clarity. However, the individual elements shown are the same as the individual elements shown and described in detail with regard to FIG. 7a and FIG. 7b.

Figures 11A, 11B, 11C, 11D, 11E, 11F, 11G, 11H:
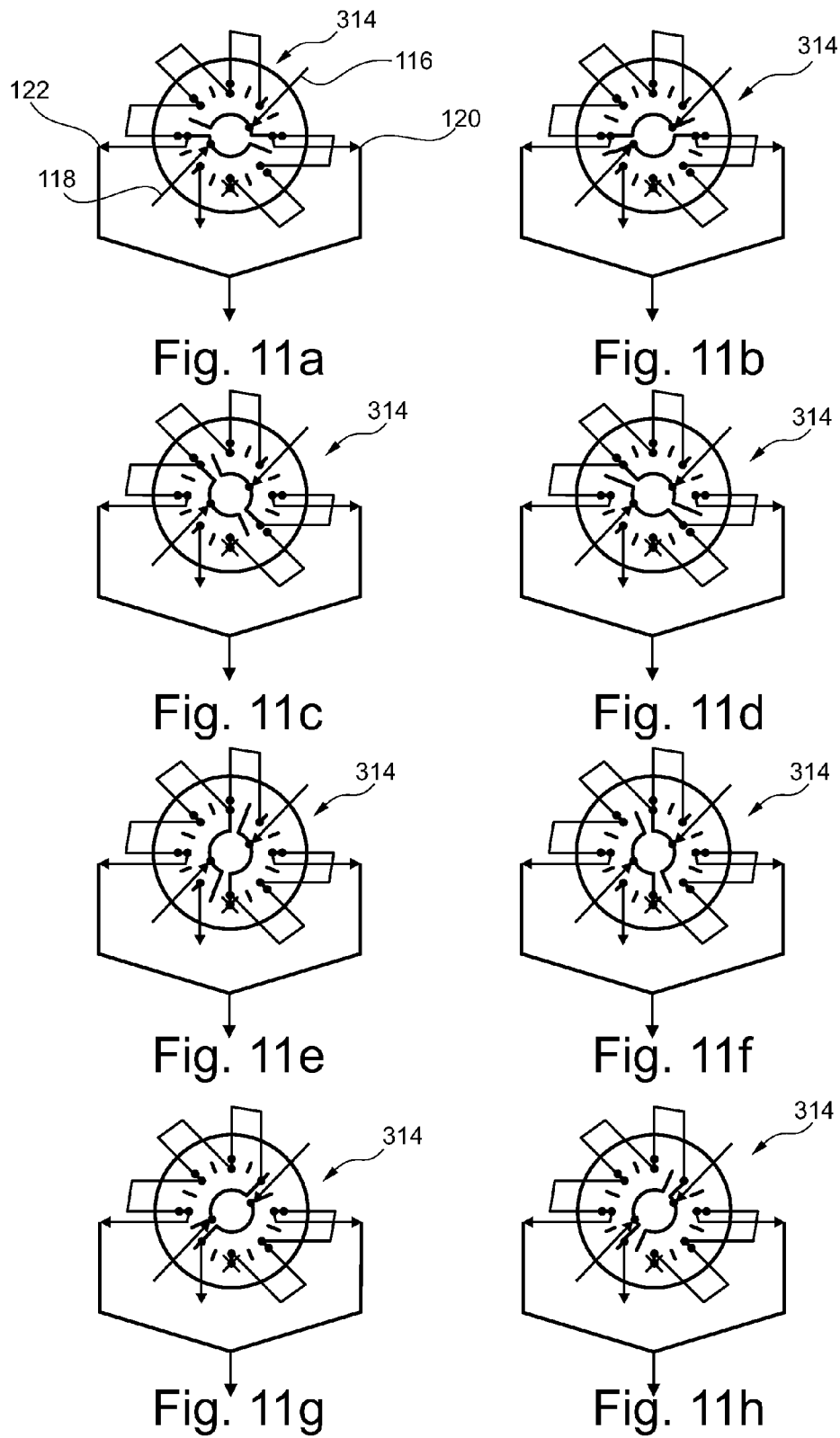
FIG. 11a to FIG. 11h show the fluidic valve of FIG. 7a and FIG. 7b in the possible switching positions.

In FIG. 11a and FIG. 11b show the valve 314 with none of the three sets of storage paths with dedicated storage path elements switched to the first inlet 116 and the second inlet 118, in accordance with embodiments of the herein disclosed subject matter.

In FIG. 11c and FIG. 11d show the valve 314 with the first set of storage paths switched to the first inlet 116 and the second inlet 118. In FIG. 11e and FIG. 11f show the valve 314 with the second set of storage paths switched to the first inlet 116 and the second inlet 118. In FIG. 11g and FIG. 11h show the valve 314 with the third set of storage paths switched to the first inlet 116 and the second inlet 118. In particular, FIG. 11g and FIG. 11h correspond to FIG. 7a and FIG. 7b.

FIG. 12a to FIG. 12h show the fluidic valve 414 of FIG. 8a and FIG. 8b in the possible switching positions. Herein, the switching positions shown on the left hand side (FIG. 12a, 12c, 12e, 12g) correspond to the first state and the switching positions shown on the right hand side (FIG. 12b, 12d, 12f, 12h) correspond to the second state. The individual elements in FIG. 12a to FIG. 12h are not labeled for the sake of clarity. However, the individual elements shown are the same as the individual elements shown and described in detail with regard to FIG. 8a and FIG. 8b.

Figure 12A:
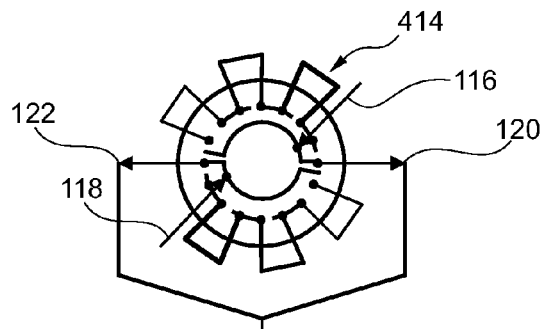
FIG. 12a to FIG. 12h show the fluidic valve of FIG. 8a and FIG. 8b in the possible switching positions.
Figure 12B:
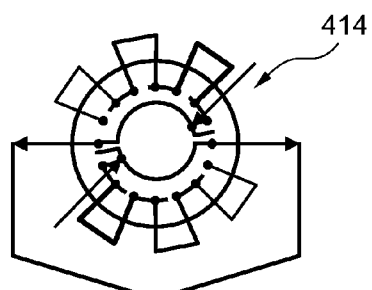

In FIG. 12a and FIG. 12b show the valve 414 with none of the three sets of storage paths with dedicated storage path elements switched to the first inlet 116 and the second inlet 118, in accordance with embodiments of the herein disclosed subject matter.

Figure 12C:
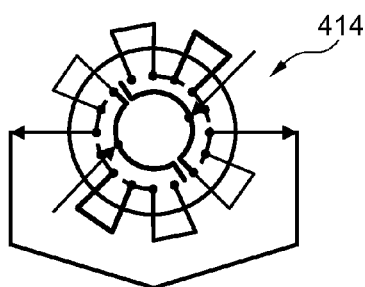
Figure 12D:
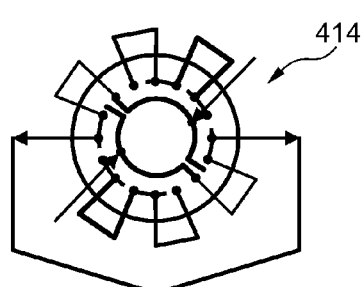
Figure 12E:
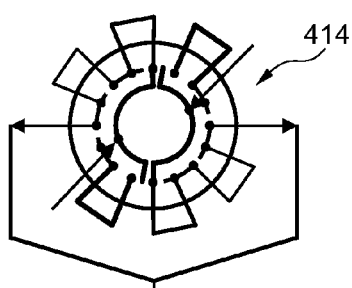
Figure 12F:
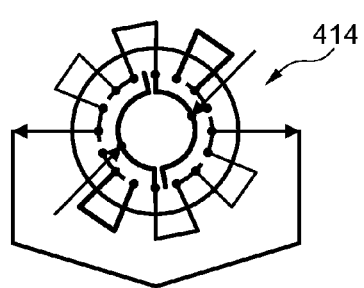
Figure 12G:
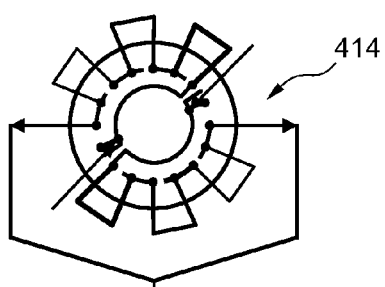
Figure 12H:
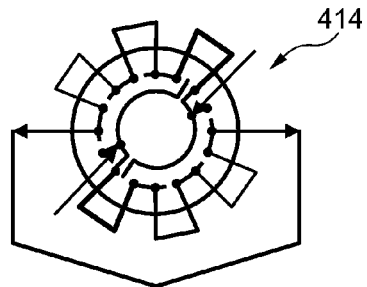

In FIG. 12c and FIG. 12d show the valve 414 with the first set of storage paths switched to the first inlet 116 and the second inlet 118. In particular, FIG. 12c and FIG. 12d correspond to FIG. 8a and FIG. 8b. In FIG. 12e and FIG. 12f show the valve 414 with the second set of storage paths switched to the first inlet 116 and the second inlet 118. In FIG. 12g and FIG. 12h show the valve 414 with the third set of storage paths switched to the first inlet 116 and the second inlet 118.

In accordance with embodiments of the herein disclosed subject matter, the term first, second and third set of storage paths relate to sets of storage paths which include a dedicated storage path element. According to an embodiment, a dedicated storage path element relates to a storage path element which is not necessarily included in a flow path extending between one of the inlets 116, 118 and one of the outlets 120, 122. Rather, the dedicated storage path element may be selectively fluidically decouplable from the respective inlet 116, 118. It should further be noted that numbering provided herein (e.g. zeroth, first, second, third, etc) is provided to identify individual elements and/or to order the individual elements. However, it should be understood that the exemplary numbering provided herein may be replaced by any other numbering/identification/ordering as long as the respective purpose according to one or more embodiments of the herein disclosed subject matter is fulfilled.

It should be noted that any embodiment disclosed herein may be combined with one or more other embodiments disclosed herein unless otherwise noted or unless technically infeasible.

It should be noted that any entity disclosed herein (e.g. element, component, fluid paths, flow paths etc.) is not limited to a dedicated entity as described in some embodiments. Rather, the disclosed subject matter may be implemented in various ways with various granularities on device level while still providing the desired functionality. Further, it should be noted that according to embodiments, a separate entity (e.g. element, component, fluid paths, flow paths etc.) may be provided for each of the functions disclosed herein. According to other embodiments, a single entity (e.g. element, component, fluid paths, flow paths etc.) is configured for providing two or more functions as disclosed herein.

It should be noted that the term "comprising" does not exclude other elements or features and the "a" or "an" does not exclude a plurality. In particular, the terms "consisting of" or "comprising among other features" are considered to be also disclosed by the term "comprising" as used herein. Also elements described in association with different embodiments may be combined. It should also be noted that reference signs in the claims shall not be construed as limiting the scope of the claims.

The invention claimed is:

1. A sample separation apparatus for separating a fluidic sample, the sample separation apparatus comprising:
   a first separation unit for separating the fluidic sample;
   a first fluid drive configured for generating a fluid flow for conducting the fluidic sample to be separated through the first separation unit;
   a second separation unit, arranged downstream of the first separation unit, for further separating the fluidic sample after treatment by the first separation unit;
   a second fluid drive configured for generating a fluid flow for conducting the fluidic sample or at least parts thereof, after treatment by the first separation unit, through the second separation unit;
   a fluidic valve having a first inlet fluidically coupled to one of the first fluid drive and the second fluid drive;
   the fluidic valve having a second inlet fluidically coupled to the other of the first fluid drive and the second fluid drive;
   the fluidic valve comprising at least two different sets of storage paths, wherein each set of storage paths comprises a first storage path; and wherein the first storage path of a first set of said at least two sets of storage paths has a first volume and the first storage path of a second set of said at least two sets of storage paths has a second volume different from the first volume;
   the fluidic valve being configured for selectively switching one set of said at least two sets of storage paths to the first inlet and the second inlet.

2. The sample separation apparatus according to claim 1, the fluidic valve further comprising:
   a first outlet and a second outlet;
   the fluidic valve being selectively switchable into a first state and a second state, optionally comprising at least one of the following features:
   in the first state the first inlet is fluidically coupled to the first outlet and the second inlet is fluidically coupled to the second outlet, wherein optionally the first inlet is fluidically coupled to the first outlet via the first storage path of the first set;
   in the second state in the first inlet is fluidically coupled to the second outlet and the second inlet is fluidically coupled to the first outlet, wherein optionally the second inlet is fluidically coupled to the first outlet via the first storage path of the first set.

3. The sample separation apparatus according to claim 2, further comprising the following feature:
   the fluidic valve being selectively switchable into the first state and into the second state for each of at least one set of said at least two sets of storage paths.

4. The sample separation apparatus according to claim 3, further comprising the following feature:
   for each of at least one first set of said at least two sets of storage paths, the first outlet and the second outlet are both fluidically coupled to the second separation unit; wherein optionally, the first outlet and the second outlet are both permanently fluidically coupled to the second separation unit.

5. The sample separation apparatus according to claim 1, the fluidic valve further comprising:
   a third outlet, wherein optionally the third outlet is a waste outlet bypassing the second separation unit;
   the fluidic valve optionally further comprising at least one of the following groups of features:
   for at least one of said sets, the fluidic valve is switchable into a third state in which the second inlet is fluidically coupled, via one of the first storage path and a second storage path of the set, to at least one of the first outlet and the second outlet and in which the first inlet is fluidically coupled to the third outlet, optionally via the other of the first storage path and the second storage path of the set;
   for at least one of said sets, the fluidic valve is switchable into a fourth state in which the first inlet is fluidically coupled, via one of the first storage path and the second storage path of the set, to at least one of the first outlet and the second outlet and in which the second inlet is fluidically coupled to the third outlet, optionally via the other of the first storage path and second storage path of the set.

6. The sample separation apparatus according to claim 2, wherein:
   at least one set of said at least two different sets of storage paths comprises a second storage path;
   wherein for each of the at least one set, if the set is switched to the first inlet and the second inlet, in the first state the first inlet is fluidically coupled to the first storage path of the set and the second inlet is fluidically coupled to the second storage path of the set; and
   wherein for each of the at least one set, if the set is switched to the first inlet and the second inlet, in the second state the first inlet is fluidically coupled to the second storage path of the selected set and the second inlet is fluidically coupled to the first storage path of the selected set.

7. The sample separation apparatus according to claim 6, further comprising:
   the fluidic valve being configured such that of the selected set of storage paths, which is switched to the first inlet and to the second inlet, the first storage path is fluidically coupled to the first outlet and the second storage path is fluidically coupled to the second outlet in both, the first state and the second state.

8. The sample separation apparatus according to claim 2, further comprising at least one of the following features:
   a first base fluid path moveable to a first position corresponding to the first state and moveable to a second position corresponding to the second state of the fluidic valve; the first base fluid path fluidically coupling the first inlet and the first outlet in the first state; the first base fluid path fluidically coupling the first inlet and the second outlet in the second state;
   a second base fluid path moveable to a first position corresponding to the first state and moveable to a second position corresponding to the second state of the fluidic valve; the second base fluid path fluidically coupling the second inlet and the second outlet in the first state; the second base fluid path fluidically coupling the second inlet and the first outlet in the second state.

9. The sample separation apparatus according to claim 8, wherein the first base fluid path comprises:
   a first port region fluidically coupled to the first inlet;
   a second port region moveable to be fluidically coupled to the first outlet in the first state and moveable to be fluidically closed in the second state; and a third port region moveable to be fluidically coupled to the second outlet in the second state and moveable to be closed in the first state, wherein the first port region, the second port region and the third port region of the first base fluid path are fluidically coupled to each other.

10. The sample separation apparatus according to claim 8, wherein the second base fluid path comprises:
a first port region fluidically coupled to the second inlet;
a second port region moveable to be fluidically coupled to the second outlet in the first state and moveable to be fluidically closed in the second state; and
a third port region moveable to be fluidically coupled to the first outlet in the second state and moveable to be closed in the first state;
wherein the first port region, the second port region and the third port region of the second base fluid path are fluidically coupled to each other.

11. The sample separation apparatus according to claim 8, further comprising at least one of the following features:
at least one of the first base fluid path and the second base fluid path being a groove in a moveable member;
the first base fluid path and the second base fluid path are provided in a single moveable member.

12. The sample separation apparatus according to claim 1, wherein the first storage path of the second set of storage paths includes at least one of the following features:
the second volume is larger than the first volume;
the first storage path of the second set of storage paths includes at least part of the first storage path of the first set of storage paths.

13. The sample separation apparatus according to claim 1, wherein, if the first storage paths of the at least two sets are ordered so as to have ascending volumes, a first storage path of a next set, which has a volume that is larger than the volume of the first storage path of each of the preceding sets, includes the first storage path of the preceding set and an additional storage path element; and wherein optionally the first storage path of the first set, of which the first storage path has the smallest volume, includes only a single storage path element.

14. The sample separation apparatus according to claim 13, the fluidic valve further comprising:
a moveable coupling element;
the moveable coupling element being moveable into at least two coupling positions of which each coupling position corresponds to a selection of one of the at least two sets of storage paths.

15. The sample separation apparatus according to claim 14, wherein each additional storage path element of the at least two sets has a first port and a second port, the fluidic valve further comprising:
the moveable coupling element having at least one coupling fluid path;
wherein in each coupling position the at least one coupling fluid path fluidically couples the storage paths elements of all preceding sets and the additional storage path element of the set corresponding to the coupling position via their first ports and their second ports, thereby providing the first storage path of the set of storage paths corresponding to the coupling position;
wherein optionally one of the first coupling fluid path and the second coupling fluid path fluidically couples the first storage path of the set of storage paths corresponding to the coupling-position to an outlet port; and
wherein optionally the at least one coupling fluid path is a groove in the moveable coupling element.

16. The sample separation apparatus according to claim 15, wherein the movement of the moveable coupling element defines a path of motion of the at least one coupling fluid path, the sample separation apparatus further comprising at least one of the following features:
the first port and the second port of each first storage path element is located in a position overlapping the path of motion of the at least one coupling fluid path;
the extent of the coupling fluid path in a direction along its path of motion is larger than the distance between the ports, to be coupled by the coupling fluid path, along the path of motion, wherein optionally of a first port and a second port to be coupled by the coupling fluid path at least a part of the first port is in line with the second port along the path of motion;
the extent of the coupling fluid path perpendicular to the path of motion is larger than the distance, perpendicular to the path of motion, between the ports to be coupled by the coupling fluid path, wherein optionally of a first port and a second port to be coupled by the coupling fluid path at least a part of the first port is in line with the second port perpendicular to the path of motion.

17. The sample separation apparatus according to claim 15, wherein at least one of the first base fluid path and the second base fluid path is provided in the moveable coupling element.

18. The sample separation apparatus according to claim 17, further comprising one of the following features:
the extent of a coupling fluid path along the path of motion of the coupling fluid path is at least the distance along the path of motion between the ports to be coupled by the coupling fluid path plus the larger one of i) the distance along the path of motion between the first position and the second position of the first base fluid path and ii) the distance along the path of motion between the first position and the second position of the second base fluid path;
the at least one coupling fluid path comprising a first coupling fluid path and a second coupling fluid path different from the first coupling fluid path; in the first position of the first base fluid path a first port and a second port are coupled by the first coupling fluid path, and in the second position of the first base fluid path the first port and the second port are coupled by the second coupling fluid path.

19. The sample separation apparatus according to claim 14, further comprising at least one of the following features:
the first base fluid path is provided in a first switching element, the first switching element being moveable with regard to the moveable coupling element in order to switch one port of two end ports of the first storage path of the selected set into fluid communication with the first base fluid path or out of fluid communication with the first base fluid path;
the second base fluid path is provided in a second switching element, the second switching element being moveable with regard to the moveable coupling element in order to switch one port of two end ports of the first storage path of the selected set into fluid communication with the second base fluid path or out of fluid communication with the second base fluid path;
wherein optionally the second switching element is the first switching element;
wherein optionally the sample separation apparatus comprises an actuator for driving the first switching element; and
wherein optionally the first switching element comprises a stop face configured to be driveable, by the actuator, into contact with a corresponding stop face on the moveable coupling element, the moveable coupling element thereby being drivable by the first switching element upon further driving of the first switching element.

20. The sample separation apparatus according to claim 14, further comprising at least one of the following features:

the moveable coupling element is rotatable and is moveable into the at least two coupling positions by rotation of the moveable coupling element; wherein optionally the moveable coupling element has at least one coupling fluid path, and the sample separation apparatus comprises the further features that the rotation of the moveable coupling element defines a circumferential direction and a radial direction perpendicular to the circumferential direction and that the at least one coupling fluid path comprises a circumferential groove section; wherein optionally the moveable coupling element has at least one coupling fluid path, and the sample separation apparatus comprises the further features that the at least one coupling fluid path comprises a radial groove extending in a radial direction;

the moveable coupling element is linearly moveable coupling element being moveable into the at least two coupling positions along a linear axis.

21. The sample separation apparatus according to claim 1, further comprising at least one of the following features:

the sample separation apparatus comprises at least one actuator for controllably moving moveable elements;

the sample separation apparatus comprises a flow coupler having two fluid inlet terminals and a fluid outlet terminal in fluid communication with one another, the fluid outlet terminal being fluidically coupled or coupleable to the second separation unit;

wherein optionally the flow coupler is configured as one of the group consisting of a fluidic T-piece, a fluidic Y-piece, and a fluidic X-piece;

wherein the first separation unit is arranged between the first fluid drive and one of the first inlet and the second inlet of the fluidic valve which fluidically couples the first fluid drive with the fluidic valve;

wherein the second separation unit is directly fluidically coupled to the fluid outlet terminal of the flow coupler;

wherein the fluidic valve is switchable so that pressure conditions in the first separation unit and in the second separation unit remain constant before and after switching;

the sample separation apparatus comprises a detector for detecting the separated fluidic sample and being arranged downstream of the second separation unit;

the sample separation apparatus comprises a sample injector for injecting the fluidic sample into a mobile phase and being arranged between the first fluid drive and the first separation unit;

wherein the first fluid drive is operable with a first flow rate being smaller than a second flow rate according to which the second fluid drive is operable; wherein optionally the second flow rate is at least five times the first flow rate;

wherein the fluidic valve is switchable for performing the separation of the fluidic sample so that the first fluid drive and the second fluid drive are in fluid communication with one another via the flow coupler in at least some of the switching states of the fluidic valve.

22. The sample separation apparatus according to claim 1, comprising a control device configured for:

controlling the first separation unit to execute a primary separation sequence within a measurement volume interval for separating the fluidic sample into a plurality of fractions;

controlling the second separation unit to execute a plurality of secondary separation sequences within the measurement volume interval for further separating at least a part of the plurality of separated fractions;

wherein optionally at least one of the primary separation sequence and the plurality of secondary separation sequences relates to a chromatographic gradient run.

23. The sample separation apparatus according to claim 1, further comprising at least one of the following:

the first separation unit and the second separation unit are configured so as to execute respective sample separations in accordance with different separation criteria;

the first separation unit and the second separation unit are configured so as to execute the respective sample separations on identical separation media but with different operating conditions.

24. The sample separation apparatus according to claim 1, comprising at least one of the following features:

the sample separation apparatus comprises a control device configured for controlling operation of at least one of: the first fluid drive, the second fluid drive, and the fluidic valve;

at least one of the first separation unit and the second separation unit is configured for performing a separation in accordance with at least one of: liquid chromatography, supercritical-fluid chromatography, capillary electrochromatography, electrophoresis, and gas chromatography;

the sample separation apparatus is configured as a two-dimensional liquid chromatography sample separation apparatus;

the sample separation apparatus is configured to analyze at least one physical, chemical and/or biological parameter of at least one compound of the fluidic sample;

the sample separation apparatus comprises at least one of: a chromatography device, a liquid chromatography device, an HPLC device, a gas chromatography device, a capillary electrochromatography device, an electrophoresis device, a capillary electrophoresis device, and a gel electrophoresis device;

the sample separation apparatus is configured for generating a fluid flow for conducting the fluidic sample with a high pressure;

the sample separation apparatus is configured for generating a fluid flow for conducting the fluidic sample with a pressure of at least 100 bar;

the sample separation apparatus is configured to conduct a liquid fluid;

the sample separation apparatus is configured as a microfluidic device;

the sample separation apparatus is configured as a nanofluidic device;

at least one of the first separation unit and the second separation unit is configured for retaining at least a part of components of the fluidic sample and for allowing other components of the fluidic sample to pass;

at least one of the first separation unit and the second separation unit comprises a separation column;

at least one of the first separation unit and the second separation unit comprises a chromatographic column;

at least a part of at least one of the first separation unit and the second separation unit is filled with a separating material.

* * * * *